US011224511B2

(12) United States Patent
Dixon et al.

(10) Patent No.: US 11,224,511 B2
(45) Date of Patent: *Jan. 18, 2022

(54) HEART VALVE SEALING DEVICES AND DELIVERY DEVICES THEREFOR

(71) Applicant: Edwards Lifesciences Corporation, Irvine, CA (US)

(72) Inventors: Eric Robert Dixon, Villa Park, CA (US); Jensen Chen, Walnut, CA (US); Guillermo W. Moratorio, Laguna Beach, CA (US); Sergio Delgado, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 15/884,193

(22) Filed: Jan. 30, 2018

(65) Prior Publication Data

US 2018/0296327 A1 Oct. 18, 2018

Related U.S. Application Data

(60) Provisional application No. 62/486,835, filed on Apr. 18, 2017.

(51) Int. Cl.
*A61F 2/24* (2006.01)
*A61B 17/128* (2006.01)
(Continued)

(52) U.S. Cl.
CPC .......... *A61F 2/246* (2013.01); *A61B 17/1227* (2013.01); *A61B 17/1285* (2013.01);
(Continued)

(58) Field of Classification Search
CPC ................. A61F 2/246; A61F 2/2466; A61F 2220/0016; A61F 2/2463;
(Continued)

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
EP 0098100 A2 1/1984
(Continued)

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.
(Continued)

*Primary Examiner* — Seema Mathew
(74) *Attorney, Agent, or Firm* — Thomas C. Richardson

(57) ABSTRACT

An implantable prosthetic device such as might be used to treat poor function of a diseased heart valve in a medical patient includes a body portion and an anchor portion including a plurality of paddles. Clasps attached to the paddles include fixed arms and moveable arms operable to secure the device to the patient's native valve leaflets.

11 Claims, 27 Drawing Sheets

(51) Int. Cl.
*A61B 17/122* (2006.01)
*A61B 17/00* (2006.01)
*A61B 17/064* (2006.01)
*A61F 2/00* (2006.01)

(52) U.S. Cl.
CPC .......... *A61F 2/2403* (2013.01); *A61F 2/2436* (2013.01); *A61F 2/2466* (2013.01); *A61B 2017/00243* (2013.01); *A61B 2017/00349* (2013.01); *A61B 2017/00783* (2013.01); *A61B 2017/00876* (2013.01); *A61B 2017/0641* (2013.01); *A61F 2/0077* (2013.01); *A61F 2210/0014* (2013.01); *A61F 2220/0008* (2013.01); *A61F 2220/0016* (2013.01); *A61F 2220/0033* (2013.01); *A61F 2220/0041* (2013.01); *A61F 2220/0075* (2013.01); *A61F 2220/0091* (2013.01); *A61F 2230/0006* (2013.01); *A61F 2230/0008* (2013.01); *A61F 2230/0013* (2013.01); *A61F 2230/0045* (2013.01); *A61F 2230/0069* (2013.01)

(58) Field of Classification Search
CPC ............ A61F 2220/0091; A61F 2/2403; A61F 2/2406; A61B 17/1227; A61B 2017/00243; A61B 2017/00783; A61B 2017/0641
See application file for complete search history.

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,875,224 B2 | 4/2005 | Grimes |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | St. Goar et al. |
| 8,029,518 B2 | 10/2011 | Goldfarb et al. |
| 8,052,592 B2 | 11/2011 | Goldfarb et al. |
| 8,052,749 B2 | 11/2011 | Salahieh et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |

(56) References Cited

U.S. PATENT DOCUMENTS

| | | |
|---|---|---|
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,926,691 B2 | 1/2015 | Chau et al. |
| 8,945,177 B2 | 2/2015 | Dell et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,138,312 B2 | 9/2015 | Tuval et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 * | 9/2018 | Metchik ............. A61F 2/246 |
| 10,099,050 B2 * | 10/2018 | Chen .................. A61N 1/362 |
| 10,105,221 B2 | 10/2018 | Siegel |
| 10,105,222 B1 * | 10/2018 | Metchik ........... A61B 17/1285 |
| 10,111,751 B1 * | 10/2018 | Metchik ............ A61F 2/2466 |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 11,096,784 B2 * | 8/2021 | Dixon .................. A61F 2/2436 |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0167539 A1 | 8/2004 | Kuehn et al. |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St. Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux et al. |
| 2007/0197858 A1 * | 8/2007 | Goldfarb ............ A61B 17/0401 600/37 |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |

(56) References Cited

U.S. PATENT DOCUMENTS

| | | |
|---|---|---|
| 2008/0147112 A1 | 6/2008 | Sheets et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0217283 A1 | 8/2010 | St. Goar et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1* | 3/2014 | Goldfarb ............ A61B 17/0401 600/37 |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1* | 10/2016 | Wei ................ A61F 2/2454 |
| 2016/0317290 A1 | 11/2016 | Chau et al. |
| 2016/0324634 A1 | 11/2016 | Gabbay |
| 2016/0331523 A1* | 11/2016 | Chau ............... A61F 2/2466 |
| 2016/0354082 A1 | 12/2016 | Oz et al. |
| 2017/0020521 A1* | 1/2017 | Krone ............... A61B 17/08 |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1* | 2/2017 | Ganesan ............ A61B 90/57 |
| 2017/0049455 A1 | 2/2017 | Seguin |
| 2017/0100236 A1 | 4/2017 | Robertson et al. |
| 2017/0105724 A1* | 4/2017 | Limem ............ A61B 17/0401 |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1* | 1/2018 | McNiven ............ A61F 2/246 623/2.11 |
| 2018/0049868 A1* | 2/2018 | Board ............... A61F 2/2403 |
| 2018/0078271 A1 | 3/2018 | Thrasher, III |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1* | 5/2018 | Hernandez ....... A61B 17/00234 |
| 2018/0153552 A1 | 6/2018 | King et al. |
| 2018/0161159 A1* | 6/2018 | Lee ................ A61B 17/122 |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1* | 10/2018 | Dixon ............... A61F 2/2436 |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1* | 10/2018 | Dixon ............... A61F 2/2436 |
| 2018/0296332 A1 | 10/2018 | Dixon et al. |
| 2018/0296333 A1 | 10/2018 | Dixon et al. |

(56) References Cited

U.S. PATENT DOCUMENTS

| | | | |
|---|---|---|---|
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |
| 2020/0237512 A1 | 7/2020 | McCann et al. |
| 2020/0337842 A1 | 10/2020 | Metchik et al. |

FOREIGN PATENT DOCUMENTS

| | | |
|---|---|---|
| EP | 0879069 B1 | 8/2003 |
| EP | 1281375 A3 | 12/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2428169 B1 | 10/2016 |
| EP | 2266503 B1 | 1/2017 |
| EP | 2266504 B1 | 3/2017 |
| FR | 2146050 A5 | 2/1973 |
| FR | 9711600 | 3/1997 |
| FR | 2 768 324 A1 | 3/1999 |
| JP | 2014000417 A | 1/2014 |
| WO | 9802103 A1 | 1/1998 |
| WO | 9900059 A1 | 1/1999 |
| WO | 9913777 A1 | 3/1999 |
| WO | 0060995 A3 | 4/2001 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006086434 A1 | 8/2006 |
| WO | 2006116558 A2 | 11/2006 |
| WO | 2006138173 A3 | 3/2007 |
| WO | 2006047709 A3 | 7/2007 |
| WO | 2008147964 A1 | 12/2008 |
| WO | 2008150529 A1 | 12/2008 |
| WO | 2009024859 A3 | 5/2009 |
| WO | 2009108942 A1 | 9/2009 |
| WO | 2009053952 A3 | 12/2009 |
| WO | 2009116041 A3 | 3/2010 |
| WO | 2010098804 A1 | 9/2010 |
| WO | 2010128502 A1 | 11/2010 |
| WO | 2011034628 A1 | 3/2011 |
| WO | 2013059747 A1 | 4/2013 |
| WO | 2016110760 A1 | 7/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |

OTHER PUBLICATIONS

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Al Zaibag et al., "Percutaneous Balloon Valvotomy in Tricuspid Stenosis", British Heart Journal, vol. 57, No. 1, Jan. 1987.

Andersen, H.R. "History of Percutaneous Aortic Valve Prosthesis," Herz No. 34. pp. 343-346. 2009.

Andersen, et al., "Transluminal implantation of artificial heart valves. Description of a new expandable aortic valve and initial results with implantation by catheter technique in closed chest pigs." European Heart Journal (1992), 13, 704-708.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., et al., "Percutaneous Endovascular Graft: Experimental Evaluation", Cardiovascular Radiology 163, pp. 357-360, May 1987.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Rosch, M.D., Josef, "The Birth, Early Years and Future of Interventional Radiology," J Vasc Interv Radiol 2003; 14:841-853.

(56) References Cited

OTHER PUBLICATIONS

Ross, D.N, "Aortic Valve Surgery", Surgery of the Aortic Valves, Guy's Hospital, London, pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

Reul RM et al., "Mitral valve reconstruction for mitral insufficiency", Prog Cardiovasc Dis., vol. 39, Issue—6, May-Jun. 1997.

Praz et a., "Compassionate use of the PASCAL transcatheter mitral valve repair system for patients with severe mitral regurgitation: a multicentre, prospective, observational, first-in-man study," Lancet vol. 390, pp. 773-780, 2017.

Batista RJ et al., "Partial left ventriculectomy to treat end-stage heart disease", Ann Thorac Surg., vol. 64, Issue—3, pp. 634-638, Sep. 1997.

Beall AC Jr. et al.,"Clinical experience with a dacron velour-covered teflon-disc mitral-valve prosthesis", Ann Thorac Surg., vol. 5, Issue 5, pp. 402-410, May 1968.

Fucci et al., "Improved results with mitral valve repair using new surgical techniques", Eur J Cardiothorac Surg. 1995;Issue 9, vol. 11, pp. 621-626.

Maisano F et al., 'The edge-to-edge technique: a simplified method to correct mitral insufficiency', Eur J Cardiothorac Surg., vol. 13, Issue—3, pp. 240-245, Mar. 1998.

Umaña JP et al., "'Bow-tie' mitral valve repair: an adjuvant technique for ischemic mitral regurgitation', Ann Thorac Surg., vol. 66, Issue—6, pp. 1640-1646, Nov. 1998.

\* cited by examiner

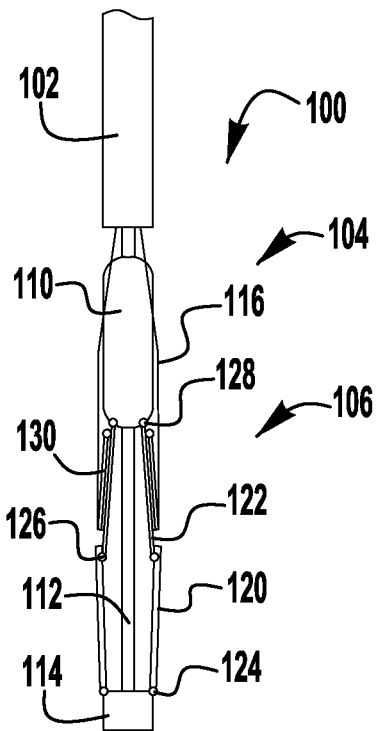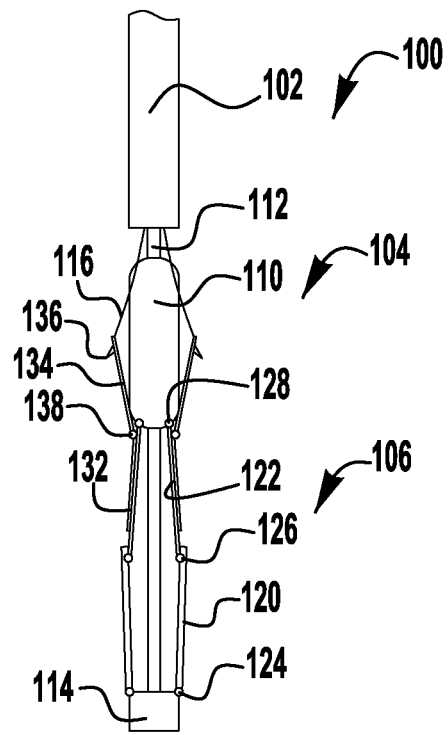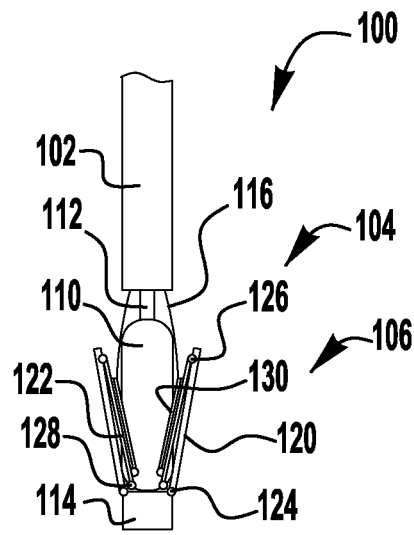

HEART VALVE SEALING DEVICES AND DELIVERY DEVICES THEREFOR

TECHNICAL FIELD

The present application relates generally to prosthetic devices and related methods for helping to seal native heart valves and prevent or reduce regurgitation therethrough, as well as devices and related methods for implanting such prosthetic devices.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a spacer implanted between the native mitral valve leaflets. Despite these prior techniques, there is a continuing need for improved devices and methods for treating mitral valve regurgitation.

BRIEF DESCRIPTION OF THE DRAWINGS

These and other features and advantages of the present invention will become better understood with regard to the following description and accompanying drawings in which:

FIGS. 1-6 show an implantable prosthetic device according to a first embodiment, in various stages of deployment;

DETAILED DESCRIPTION

Figure 3:
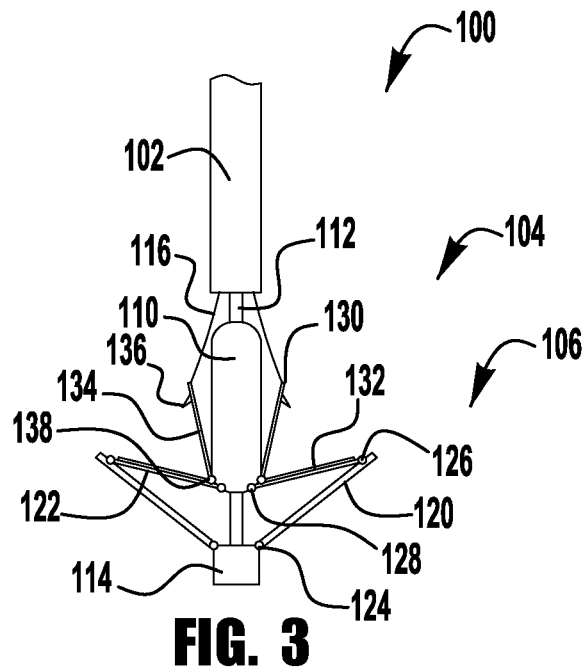

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

A prosthetic spacer device has spacer body and at least one anchor. The body is configured to be positioned within the native mitral valve orifice to help form a more effective seal between the native leaflets, thereby reducing or preventing mitral regurgitation. The body can have a structure that is impervious to blood and that allows the native leaflets to close around the sides of the body during ventricular systole to block blood from flowing from the left ventricle back into the left atrium. The body is sometimes referred to herein as a spacer because the body can fill a space between improperly functioning native mitral leaflets that do not close completely.

The body can have various shapes. In some embodiments, the body can have an elongated cylindrical shape having a round cross-sectional shape. In other embodiments, the body can have an oval cross-sectional shape, a crescent cross-sectional shape, or various other non-cylindrical shapes. The body can have an atrial or upper end positioned in or adjacent to the left atrium, a ventricular or lower end positioned in or adjacent to the left ventricle, and an annular side surface that extends between the native mitral leaflets.

The anchor can be configured to secure the device to one or both of the native mitral leaflets such that the body is positioned between the two native leaflets. In some embodiments, the anchor can attach to the body at a location adjacent the ventricular end of the body. In some embodiments, the anchor can attach to a shaft, to which the body is also attached. In some embodiments, the anchor and the body can be positioned independently with respect to each other by separately moving each of the anchor and the body along the longitudinal axis of the shaft. In some embodiments, the anchor and the body can be positioned simultaneously by moving the anchor and the body together along the longitudinal axis of the shaft. The anchor can be configured to be positioned behind a native leaflet when implanted such that the leaflet is captured by the anchor.

The prosthetic device can be configured to be implanted via a delivery sheath. The body and the anchor can be compressible to a radially compressed state and can be self-expandable to a radially expanded state when compressive pressure is released. The device can be configured to allow the anchor to self-expand radially away from the still-compressed body initially in order to create a gap between the body and the anchor. A native leaflet can then be positioned in the gap. The body can then be allowed to self-expand radially, closing the gap between the body and the anchor and capturing the leaflet between the body and the anchor. The implantation methods for various embodiments can be different, and are more fully discussed below with respect to each embodiment. Additional information regarding these and other delivery methods can be found in U.S. Pat. No. 8,449,599 and U.S. Patent Application Publication Nos. 2014/0222136, and 2014/0067052, 2016/0331523 each of which is incorporated herein by reference in its entirety.

The disclosed prosthetic devices are prevented from atrial embolization by having the anchor hooked to a leaflet, taking advantage of the tension from native chordae tendineae to resist high systolic pressure urging the device toward the left atrium. During diastole, the devices can rely on the compressive and retention forces exerted on the leaflet that is captured by the anchor to resist embolization into the left ventricle.

Referring now to FIGS. 1-6, an implantable prosthetic device 100 is shown in various stages of deployment. The device 100 is deployed from a delivery sheath 102 and includes a body portion 104 and an anchor portion 106. The body portion 104 of the device includes a spacer 110 for implantation between the leaflets of the native mitral valve that is slideably attached to an actuation wire or shaft 112. Actuation of the actuation wire 112 opens and closes the anchor portion 106 of the device 100 to capture the mitral valve leaflets during implantation. The actuation wire or shaft 112 may take a wide variety of different forms. For example, the actuation wire or shaft may be threaded such that rotation of the actuation wire or shaft moves the anchor portion 106 relative to the body portion 104. Or, the actuation wire or shaft may be unthreaded, such that pushing or pulling the actuation wire or shaft 112 moves the anchor portion 106 relative to the body portion 104.

The anchor portion 106 of the device 100 includes outer paddles 120 and inner paddles 122 that are connected between a cap 114 and the spacer 110 by hinged portions 124, 126, 128. The actuation wire 112 extends through the delivery sheath and the spacer 110 to the cap 114 at the distal end of the anchor portion 106. Extending and retracting the actuation wire 112 increases and decreases the spacing between the spacer 110 and the cap 114, respectfully. A collar (not shown) removably attaches the spacer 100 to the delivery sheath 102 so that the spacer 100 slides along the actuation wire 112 during actuation to open and close the paddles 120, 122 of the anchor portion 106.

Referring to FIG. 3, the barbed clasps 130 include a base or fixed arm 132, a moveable arm 134, barbs 136, and a hinge portion 138. The fixed arms 132 are attached to the inner paddles 122, with the hinge portion 138 disposed proximate the spacer 110. The hinge portion 138 provides a spring force between the fixed and moveable arms 132, 134 of the barbed clasp 130. The hinge portion 138 can be any suitable hinge, such as a flexible hinge, a spring hinge, a pivot hinge, or the like. In certain embodiments, the hinge portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs 136. The barbed clasps 130 are opened by applying tension to actuation lines 116 attached to the ends of the moveable arms 134, thereby causing the moveable arms 134 to pivot on the hinge portions 138.

During implantation, the paddles 120, 122 are opened and closed to capture the native mitral valve leaflets between the paddles 120, 122 and the spacer 110. The barbed clasps 130 further secure the native leaflets by engaging the leaflets with barbs 136 and pinching the leaflets between the moveable and fixed arms 134, 132. The barbs 136 of the barbed clasps 130 increase friction with the leaflets, or may partially or completely puncture the leaflets. The actuation lines 116 can be actuated independently so that each barbed clasp 130 can be opened and closed independently. Independent operation allows one leaflet to be captured at a time, or for the repositioning of a clasp 130 on a leaflet that was insufficiently captured, without altering a successful grasp on the other leaflet. The barbed clasps 130 not only open and close independent from each other, but can fully be opened and closed independent from the position of the inner paddle 122, thereby allowing leaflets to be captured in a variety of positions as the particular situation requires.

The barbed clasps 130 can be opened independently by pulling on an attached actuation line or suture 116 that extends through the delivery sheath 102 to the end of the barbed clasp 130. The barbed clasps 130 can be spring loaded so that in the closed position the barbed clasps 130 continue to provide a pinching force on the captured native leaflet. This pinching force remains constant regardless of the position of the inner paddles 122. Barbs 136 of the barbed clasps 130 pierce the native leaflets to further secure the native leaflets.

Referring now to FIG. 1, the device 100 is shown in an elongated or fully open condition for deployment from the delivery sheath. In the elongated condition the cap 114 is spaced apart from the spacer 110 such that the paddles 120, 122 of the anchor portion 106 are inverted or fully open. In some embodiments, an angle formed between the interior of the outer and inner paddles 120, 122 is approximately 180 degrees. The barbed clasps 130 are kept in a closed condition during deployment through the delivery sheath 102 so that the barbs 136 (FIG. 3) do not catch or damage the sheath or tissue in the patient's heart.

Referring now to FIG. 1A, the device 100 is shown in an elongated detangling condition, similar to FIG. 1, but with the barbed clasps 130 in a fully open position, up to about 180 degrees. Fully opening the device 100 and the clasps 130 has been found to improve ease of detanglement from anatomy of the patient during implantation of the device 100.

Referring now to FIG. 2, the device 100 is shown in a shortened or fully closed condition. The compact size of the device 100 in the shortened condition allows for easier maneuvering and placement within the heart. To move the device 100 from the elongated condition to the shortened condition, the actuation wire 112 is retracted to pull the cap 114 towards the spacer 110. The hinges 126 between the outer paddle 120 and inner paddle 122 are limited in movement such that compression forces acting on the outer paddle 120 from the cap 114 being retracted towards the spacer 110 cause the paddles 120, 122 to move radially outward. During movement from the open to closed position, the outer paddles 120 maintain an acute angle with the actuation wire 112. In certain embodiments, the hinge portion 124 is a spring loaded hinge that biases the outer paddles 120 in a closing direction. The acute angle maintained between the actuation wire 112 and the outer paddles 120 reduces strain on the spring loaded hinge 124. The inner paddles 122 during the same motion move through a considerably larger angle as they are oriented away from the spacer 110 in the open condition and collapse along the sides of the spacer 110 in the closed condition. In certain embodiments, the inner paddles 122 are thinner than the outer paddles, and the hinge portions 126, 128 connected to the inner paddles 122 are thinner to allow more movement than the hinge portion 124 connecting the outer paddle 124 to the cap 114.

Figure 4:
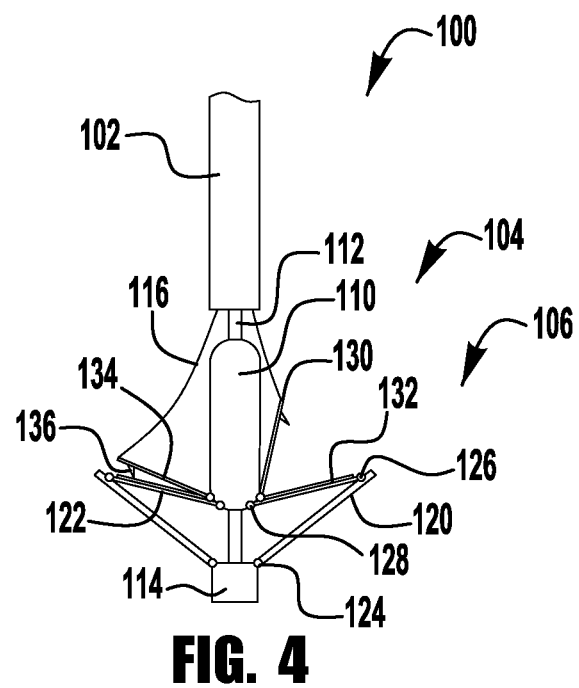
Figure 5:
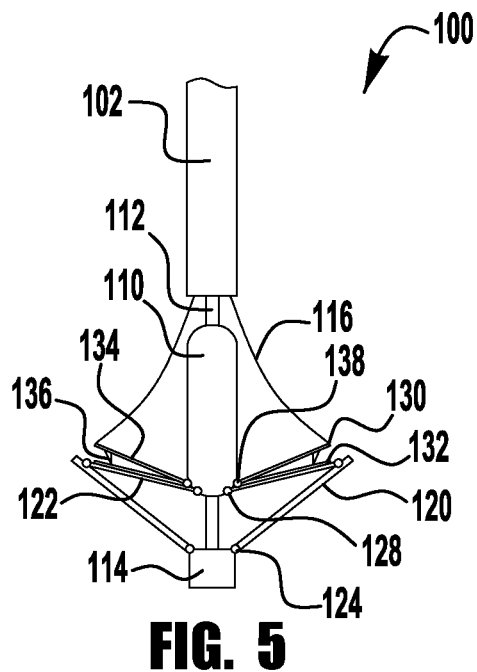

Referring now to FIGS. 3-5, the device 100 is shown in a partially open, capture-ready condition. To transition from the fully closed to the partially open condition, the actuation wire 112 is extended to push the cap 114 away from the spacer 110, thereby pulling on the outer paddles 120, which in turn pulls on the inner paddles 122, causing the anchor portion 106 to partially unfold. The actuation lines 116 are also retracted to open the clasps 130 so that the leaflets can be captured.

Referring now to FIG. 4, one of the actuation lines 116 is extended to allow one of the clasps 130 to close. Referring now to FIG. 5, the other actuation line 116 is extended to allow the other clasp 130 to close. Either or both of the actuation lines 116 may be repeatedly actuated to repeatedly open and close the barbed clasps 130.

Figure 6:
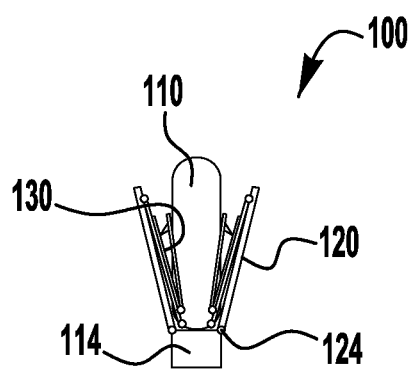

Referring now to FIG. 6, the device 100 is shown in a fully closed and deployed condition. The delivery sheath 102 and actuation wire 112 are retracted and the paddles 120, 122 and clasps 130 remain in a fully closed position. Once deployed, the device 100 may be maintained in the fully closed position with a mechanical latch, or may be biased to remain closed through the use of spring materials, such as steel, other metals, plastics, composites, etc. or shape-memory alloys such as Nitinol. For example, the hinged portions 124, 126, 128, 138 may be formed of metals such as steel or shape-memory alloy, such as Nitinol—produced in a wire, sheet, tubing, or laser sintered powder—and are biased to hold the outer paddles 120 closed around the spacer 110 and the barbed clasps 130 pinched around native leaflets. Similarly, the fixed and moveable arms 132, 134 of the barbed clasps 130 are biased to pinch the leaflets. In certain embodiments, the hinge portions 124, 126, 128, 138 may be formed of any other suitably elastic material, such as a metal or polymer material, to maintain the device in the closed condition after implantation.

Figure 7:
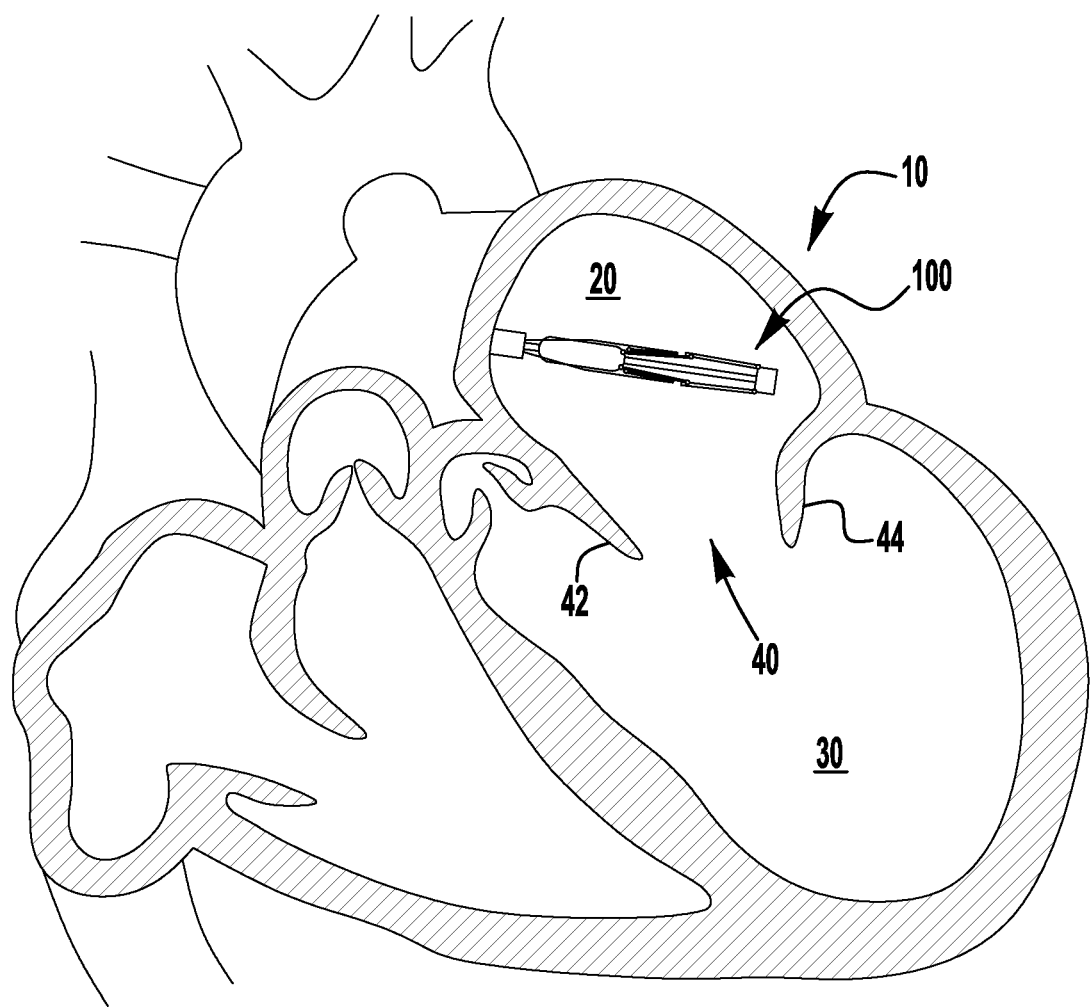
FIGS. 7-12 show the implantable prosthetic device of FIGS. 1-6 being delivered and implanted within the native mitral valve.
Figure 8:
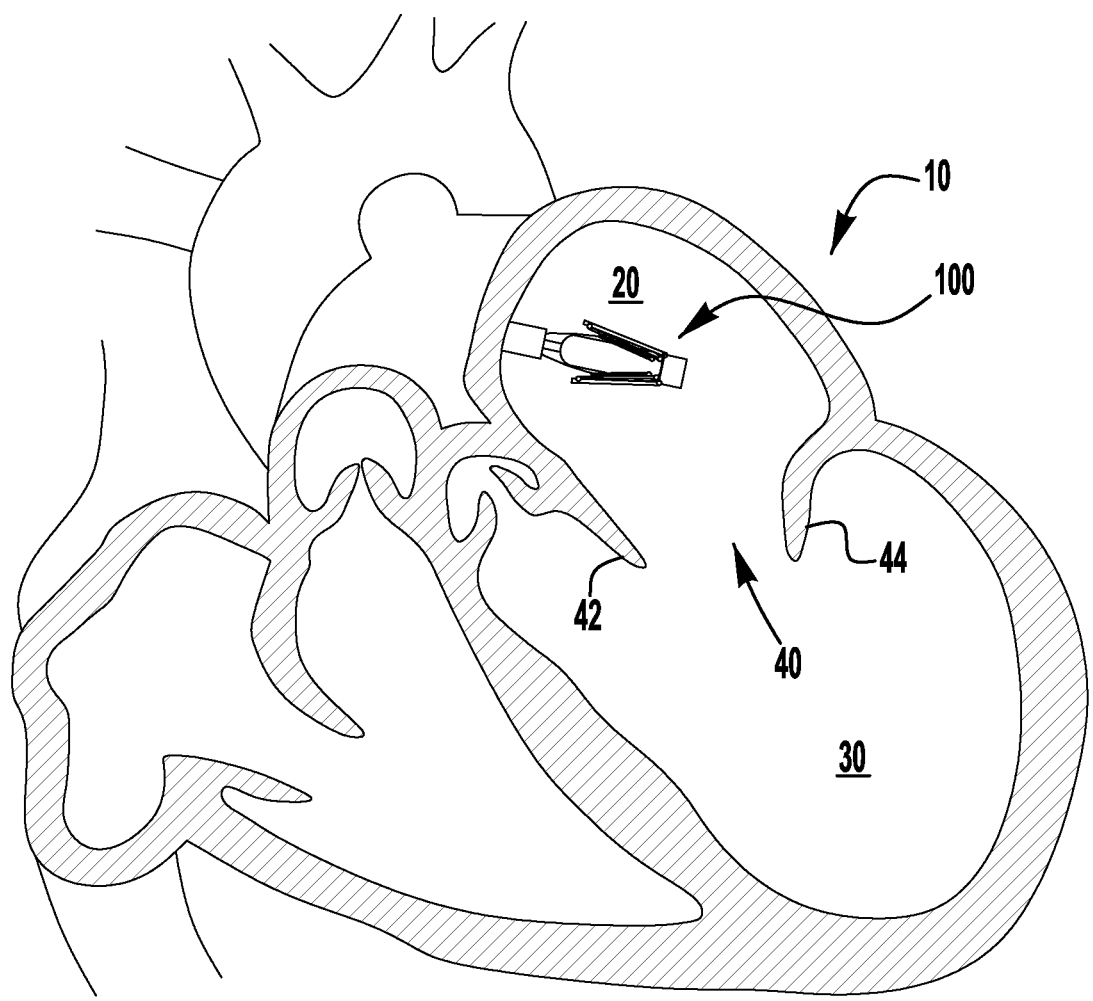
Figure 9:
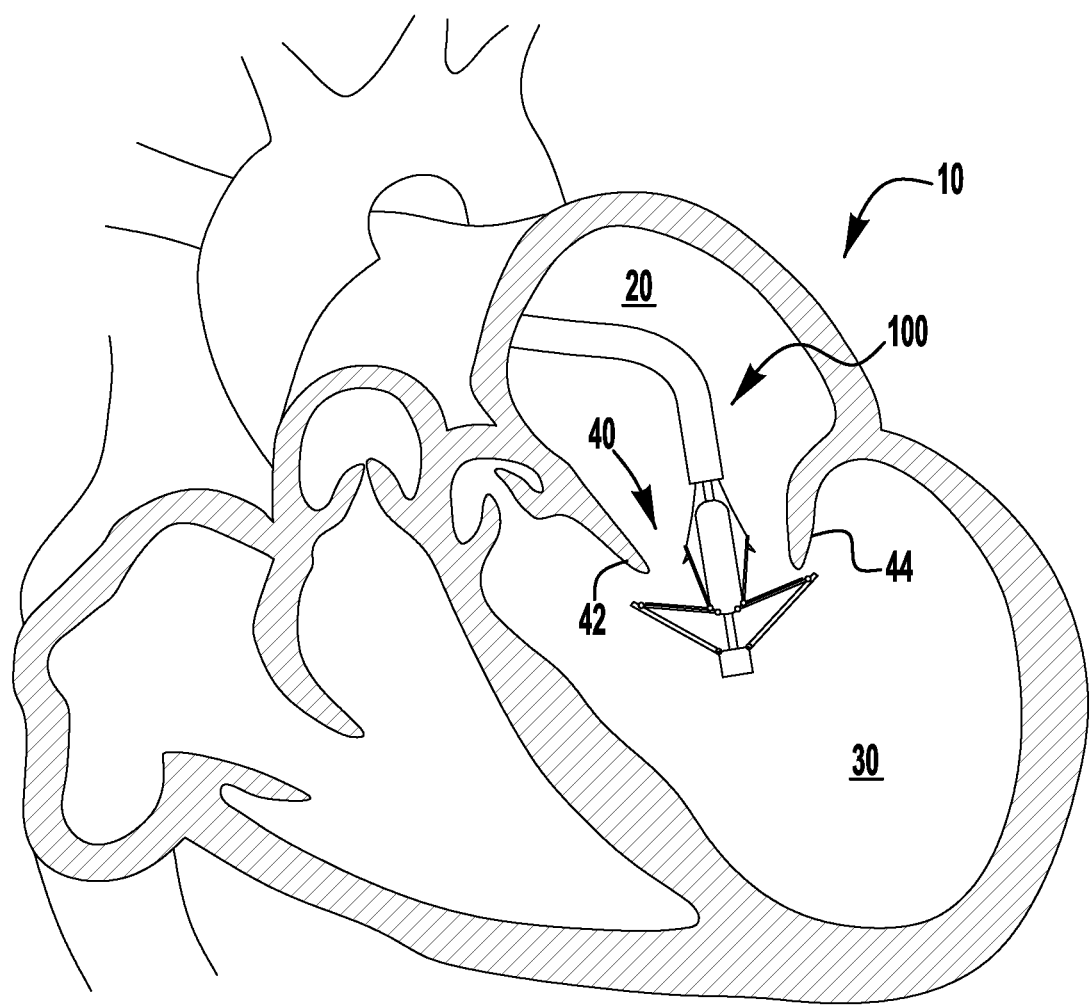
Figure 10:
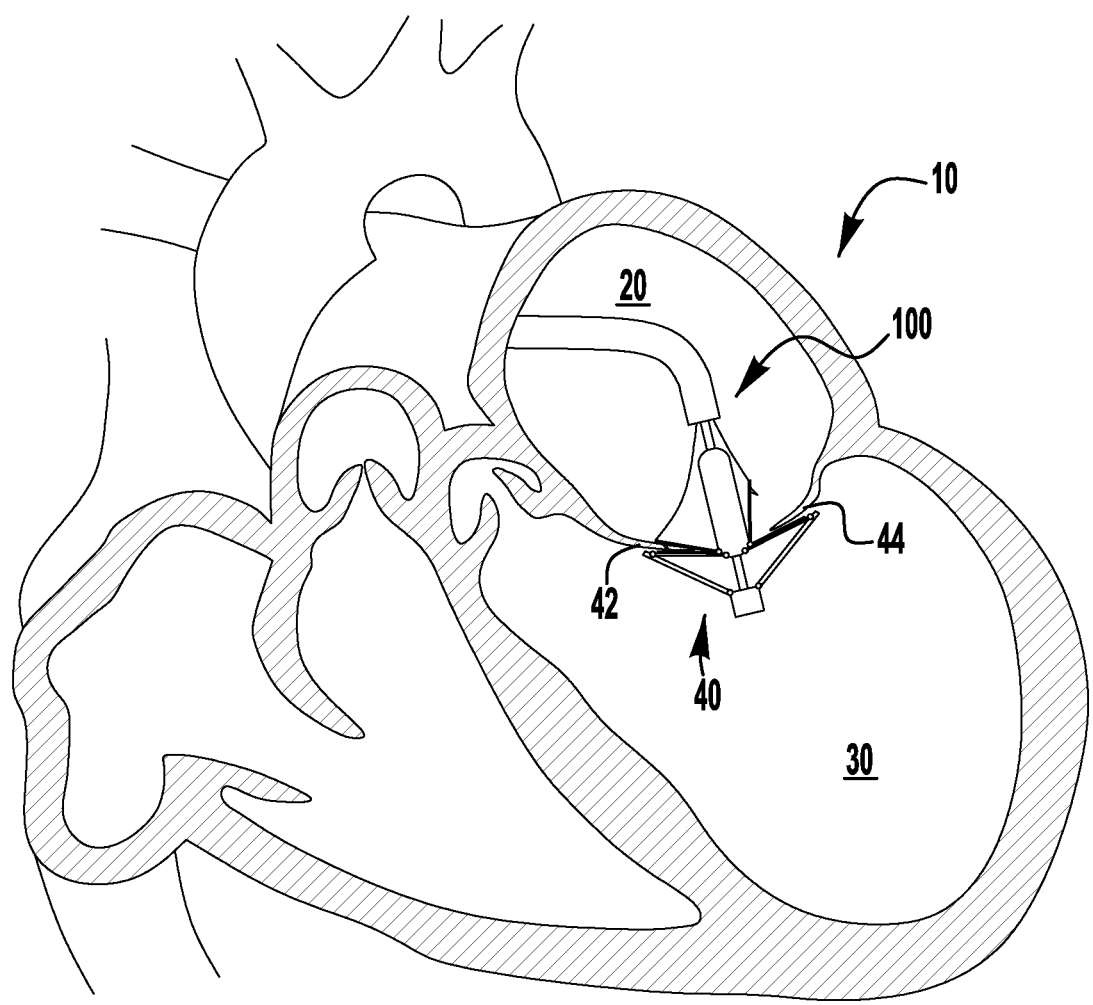
Figure 11:
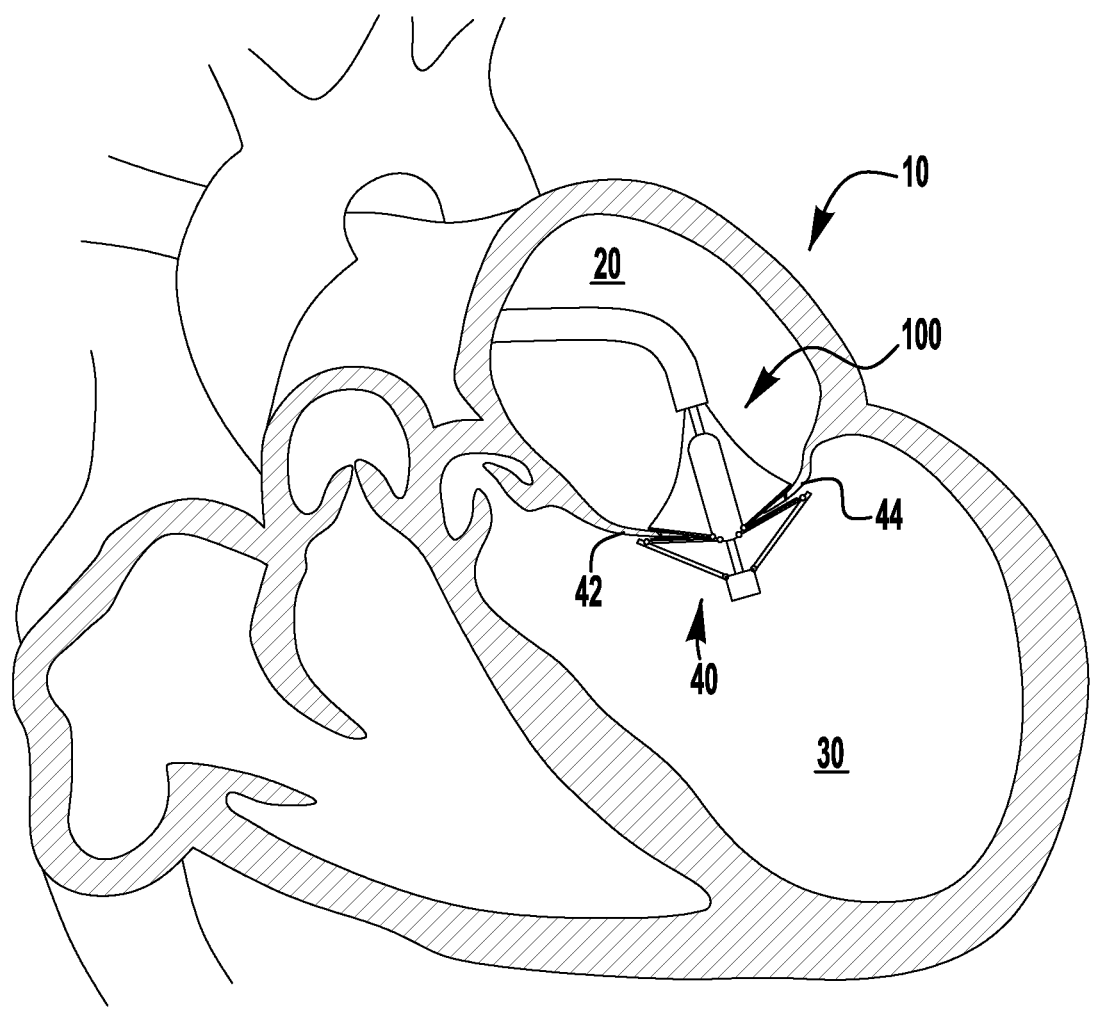
Figure 12:
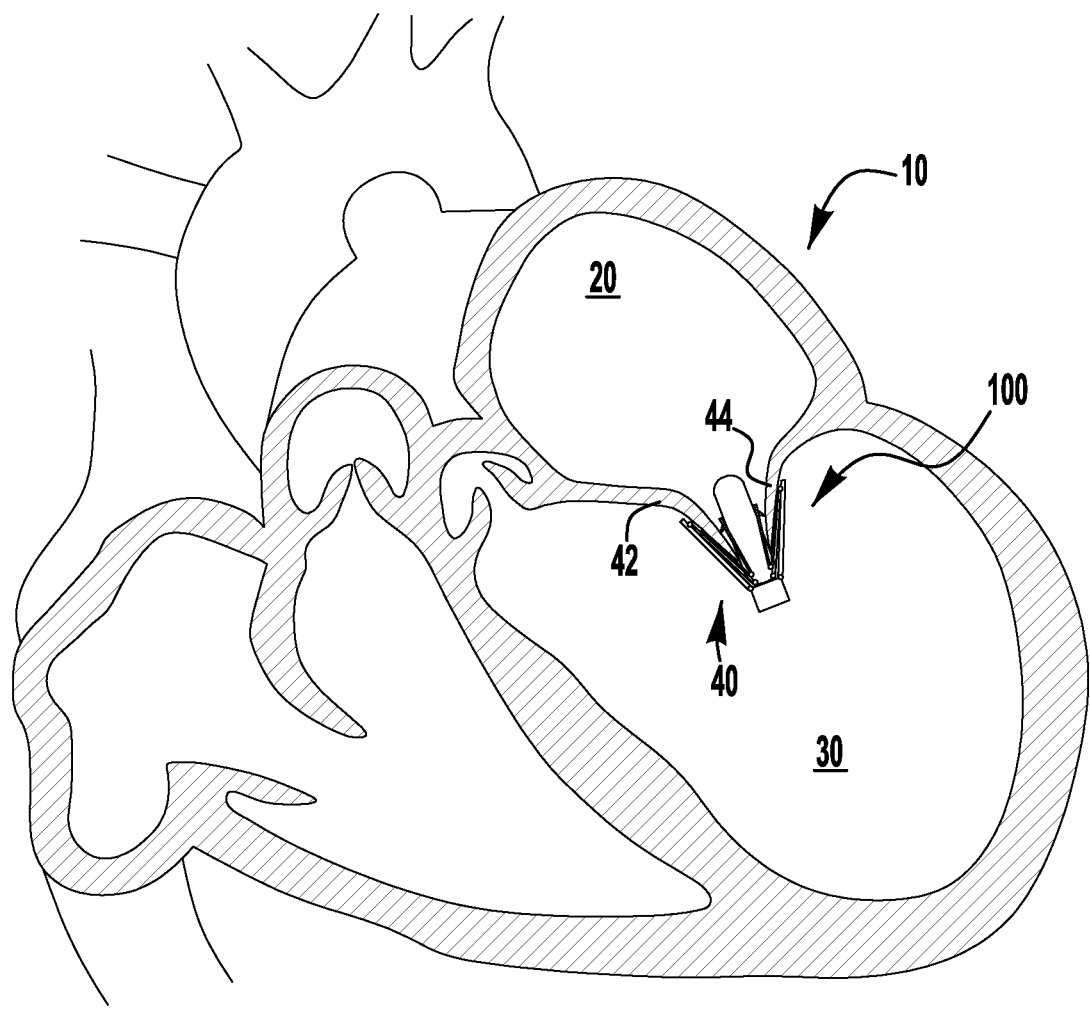

Referring now to FIGS. 7-12, the implantable device 100 of FIGS. 1-6 is shown being delivered and implanted within a native mitral valve 40 of a heart 10. Referring now to FIG. 7, the delivery sheath is inserted into the left atrium 20 through the septum and the device 100 is deployed from the delivery sheath in the fully open condition. The actuation wire 112 is then retracted to move the device 100 into the fully closed condition shown in FIG. 8. As can be seen in FIG. 9, the device 100 is moved into position within the mitral valve 40 into the ventricle 30 and partially opened so that the leaflets 42, 44 can be captured. Referring now to FIG. 10, an actuation line 116 is extended to close one of the clasps 130, capturing a leaflet 42. FIG. 11 shows the other actuation line 116 being then extended to close the other clasp 130, capturing the remaining leaflet 44. Lastly, as can be seen in FIG. 12, the delivery sheath 102 and actuation wire 112 are then retracted and the device 100 is fully closed and deployed in the native mitral valve 400.

Figure 13:
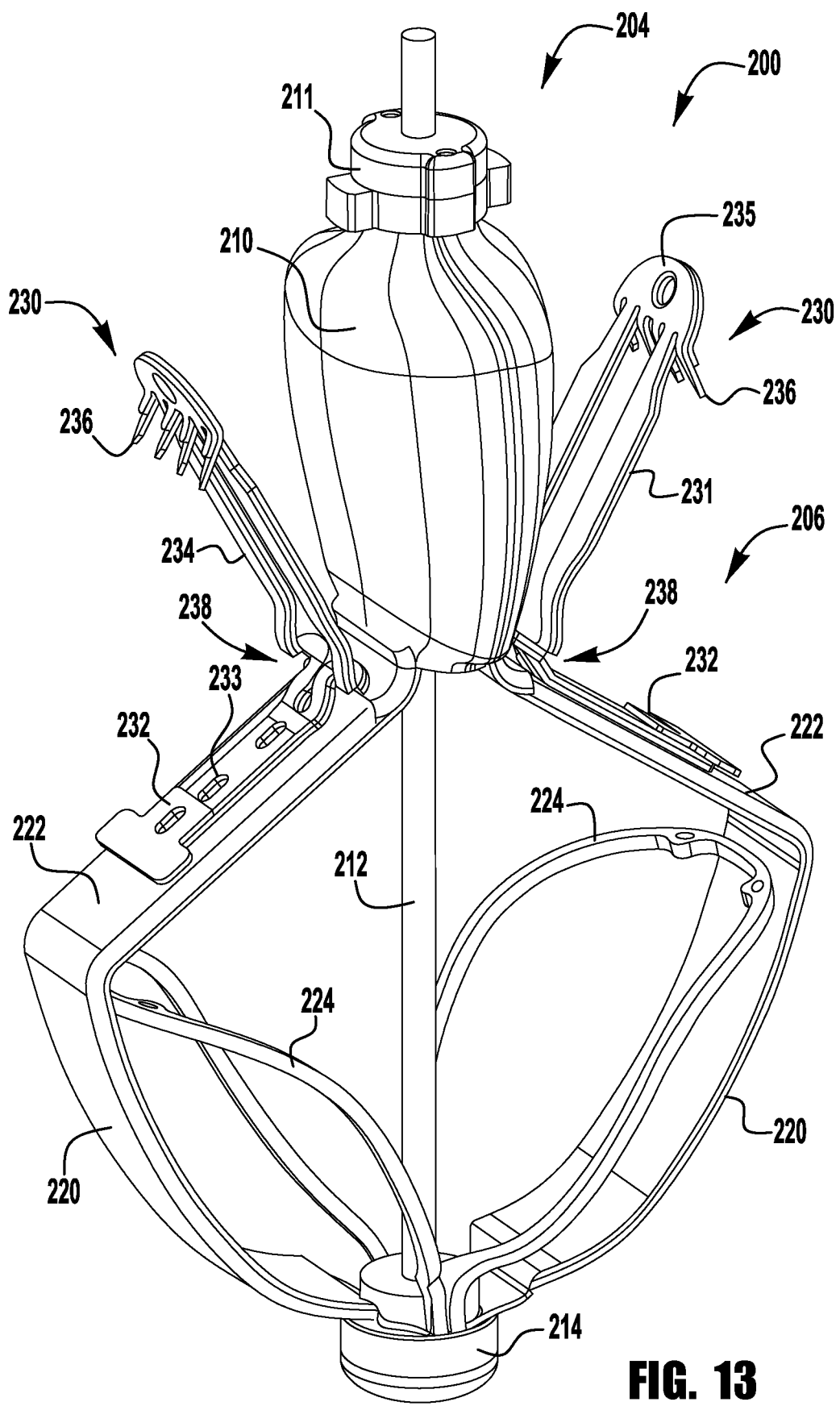
FIG. 13 shows another implantable prosthetic device according to a second embodiment.

Referring now to FIG. 13, an implantable prosthetic device 200 is shown. The device 200 is deployed from a delivery sheath (not shown) and includes a body portion 204 and an anchor portion 206. The body portion 204 of the device includes a spacer 210 for implantation between the leaflets of the native mitral valve that is slideably attached to an actuation wire or shaft 212. Actuation of the actuation wire 212 opens and closes the anchor portion 206 of the device 200 to capture the mitral valve leaflets during implantation.

The anchor portion 206 of the device 200 includes outer paddles 220 and inner paddles 222 that are hingeably connected to the cap 214 and the spacer 210. The actuation wire 212 extends through a collar (not shown), delivery sheath, and the spacer 210 to the cap 214 at the distal end of the anchor portion 206. Extending and retracting the actuation wire 212 increases and decreases the spacing between the spacer 210 and the cap 214, respectively. The collar removably engages and attaches to an upper end 211 of the spacer 200 to the delivery sheath so that the spacer 210 slides along the actuation wire 212 during actuation to open and close the paddles 220, 222 of the anchor portion 206. In some embodiments, the collar is held closed around the upper end 211 by the actuation wire 212, such that removal of the actuation wire 212 allows fingers (not shown) of the collar to open, releasing the spacer 210.

The spacer 210 and paddles 220, 222 are formed from a covering that may be a mesh, woven, braided, or formed in any other suitable way. The covering may be cloth, shape-memory alloy wire—such as Nitinol—to provide shape setting capability, or any other flexible material suitable for implantation in the human body. Paddle frames 224 provide additional pinching force between the outer paddles 222 and the spacer 210, and assist in wrapping the leaflets around the sides of the spacer 210 for a better seal between the spacer 210 and the leaflets. In some embodiments, the covering extends around the paddle frames 224.

The barbed clasps 230 include a base or fixed arm 232, a moveable arm 234, barbs 236, and a hinge portion 238. The fixed arms 232 are attached to the inner paddles 222, with the hinge portion 238 disposed proximate the spacer 210. Sutures (not shown) attach the fixed arms 232 to the inner paddles 222 through holes or slots 233. The fixed arms 232 remain stationary relative to the inner paddles 222 when the moveable arms 234 are opened to open the barbed clasps 230 and expose the barbs 236. The barbed clasps 230 are opened by applying tension to actuation lines (not shown) attached to holes 235 disposed at ends of the moveable arms 234, thereby causing the moveable arms 234 to pivot on the hinge portions 238.

During implantation, the paddles 220, 222 are opened and closed to capture the native mitral valve leaflets between the paddles 220, 222 and the spacer 210. The barbed clasps 230 further secure the native leaflets by engaging the leaflets with barbs 236 and pinching the leaflets between the moveable and fixed arms 234, 232. The barbs 236 of the barbed clasps 230 increase friction with the leaflets, or may partially or completely puncture the leaflets. The actuation lines can be actuated independently so that each barbed clasp 230 can be opened and closed independently. Independent operation allows one leaflet to be captured at a time, or for the repositioning of a clasp 230 on a leaflet that was insufficiently captured, without altering a successful grasp on the other leaflet. The barbed clasps 230 not only open and close independent from each other, but can be fully opened and closed independent from the position of the inner paddle 222, thereby allowing leaflets to be captured in a variety of positions as the particular situation requires.

Referring now to FIGS. 14-25, an implantable device 300 is shown being delivered and implanted within the native mitral valve 40 of the heart 10. The device 300 is similar to implantable device 200 of FIG. 13, though device 300 has a covering that extends around the outer paddles 320. The device 300 is deployed from a delivery sheath 302 and includes a body portion 304 and an anchor portion 306. The body portion 304 of the device includes a spacer 310 for implantation between the leaflets of the native mitral valve that is slideably attached to an actuation wire or shaft 312. Actuation of the actuation wire 312 opens and closes the anchor portion 306 of the device 300 to capture the mitral valve leaflets during implantation.

The anchor portion 306 of the device 300 includes outer paddles 320 and inner paddles 322 that are hingeably connected to the cap 314 and the spacer 310. The actuation wire 312 extends through a collar 303 (see FIG. 20), delivery sheath 302, and the spacer 310 to the cap 314 at the distal end of the anchor portion 306. Extending and retracting the actuation wire 312 increases and decreases the spacing between the spacer 310 and the cap 314, respectfully. Fingers of the collar 303 removably attach the spacer 300 to the delivery sheath 302 so that the spacer 310 slides along the actuation wire 312 during actuation to open and close the paddles 320, 322 of the anchor portion 306. In some embodiments, the collar 303 is held closed around the spacer 310 by the actuation wire 312, such that removal of the actuation wire 312 allows the fingers of the collar 303 to open, releasing the spacer 310.

The spacer 310 and paddles 320, 322 are formed from a covering that may be a mesh, woven, braided, or formed in any other suitable way. The covering may be cloth, shape-memory alloy wire—such as Nitinol—to provide shape setting capability, or any other flexible material suitable for implantation in the human body.

The barbed clasps 330 include a base or fixed arm 332, a moveable arm 334, barbs 336 (see FIG. 20), and a hinge portion 338. The fixed arms 332 are attached to the inner paddles 322, with the hinge portion 338 disposed proximate the spacer 310. Sutures (not shown) attach the fixed arms 332 to the inner paddles 322. The fixed arms 332 remain stationary when the moveable arms 334 are opened to open the barbed clasps 330 and expose the barbs 336. The barbed clasps 330 are opened by applying tension to actuation lines 316 attached to the ends of the moveable arms 334, thereby causing the moveable arms 334 to pivot on the hinge portions 338.

During implantation, the paddles 320, 322 are opened and closed to capture the native mitral valve leaflets between the paddles 320, 322 and the spacer 310. The outer paddles 320 have a wide curved shape that fits around the curved shape of the spacer 310 to more securely grip the leaflets. The curved shape and rounded edges of the outer paddle 320 also prohibits tearing of the leaflet tissue. The barbed clasps 330 further secure the native leaflets by engaging the leaflets with barbs 336 and pinching the leaflets between the moveable and fixed arms 334, 332. The barbs 336 of the barbed clasps 330 increase friction with the leaflets, or may partially or completely puncture the leaflets. The actuation lines can be actuated independently so that each barbed clasp 330 can be opened and closed independently. Independent operation allows one leaflet to be captured at a time, or for the repositioning of a clasp 330 on a leaflet that was insufficiently captured, without altering a successful grasp on the other leaflet. The barbed clasps 330 not only open and close independent from each other, but can be fully opened and closed independent from the position of the inner paddle 322, thereby allowing leaflets to be captured in a variety of positions as the particular situation requires.

Figure 14:
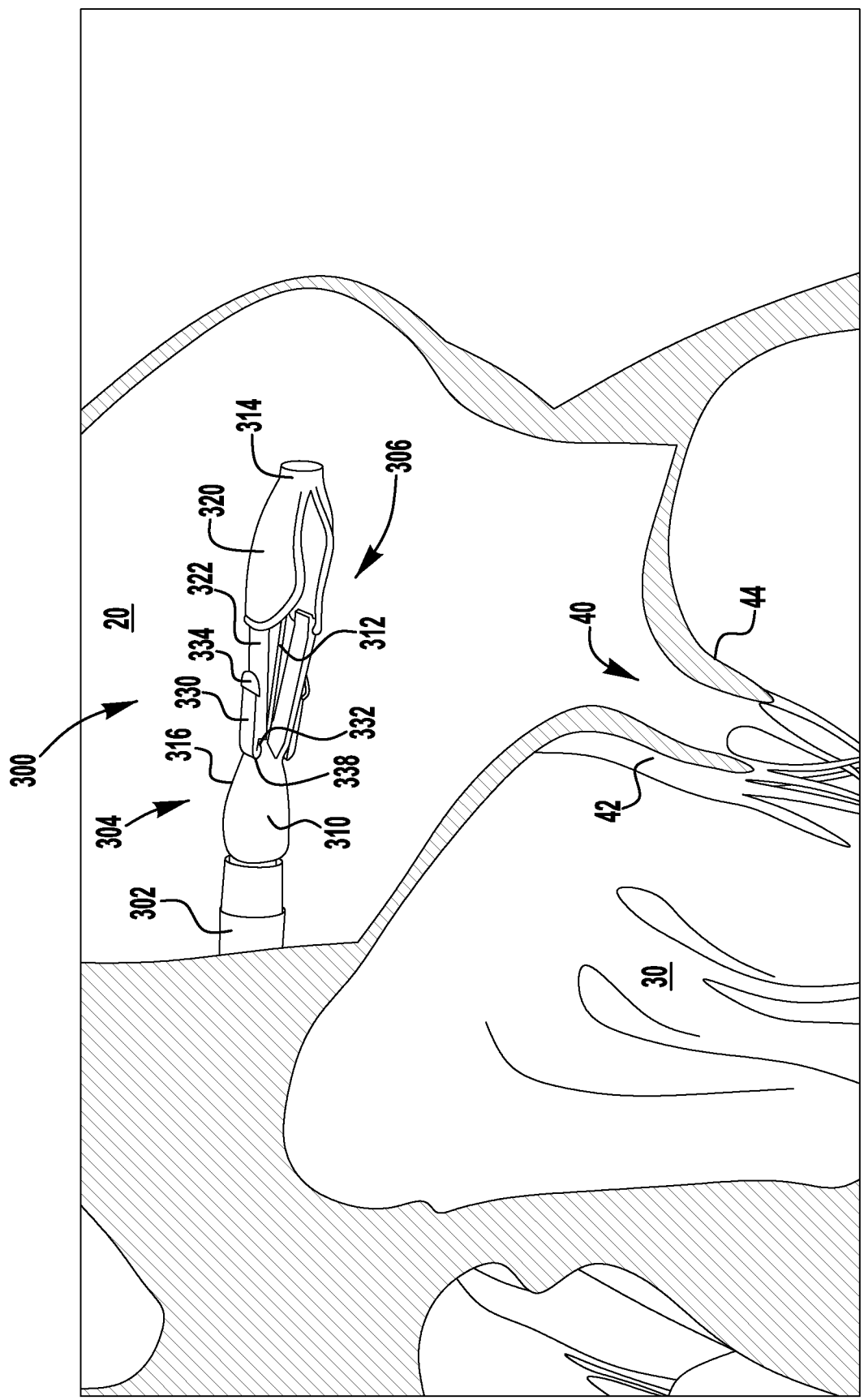
FIGS. 14-25 show another implantable prosthetic device according to a third embodiment being delivered and implanted within the native mitral valve.
Figure 15:
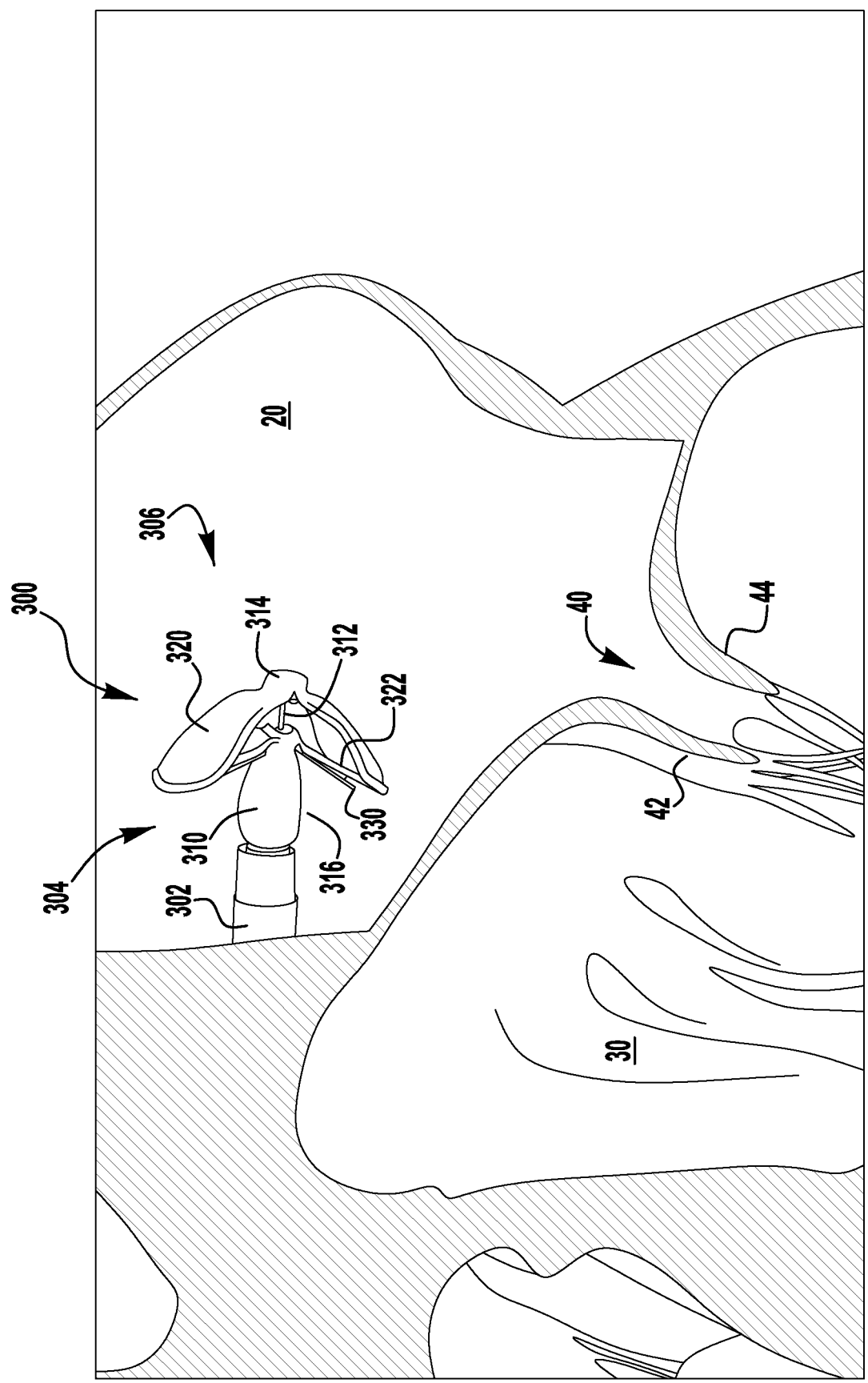
Figure 16:
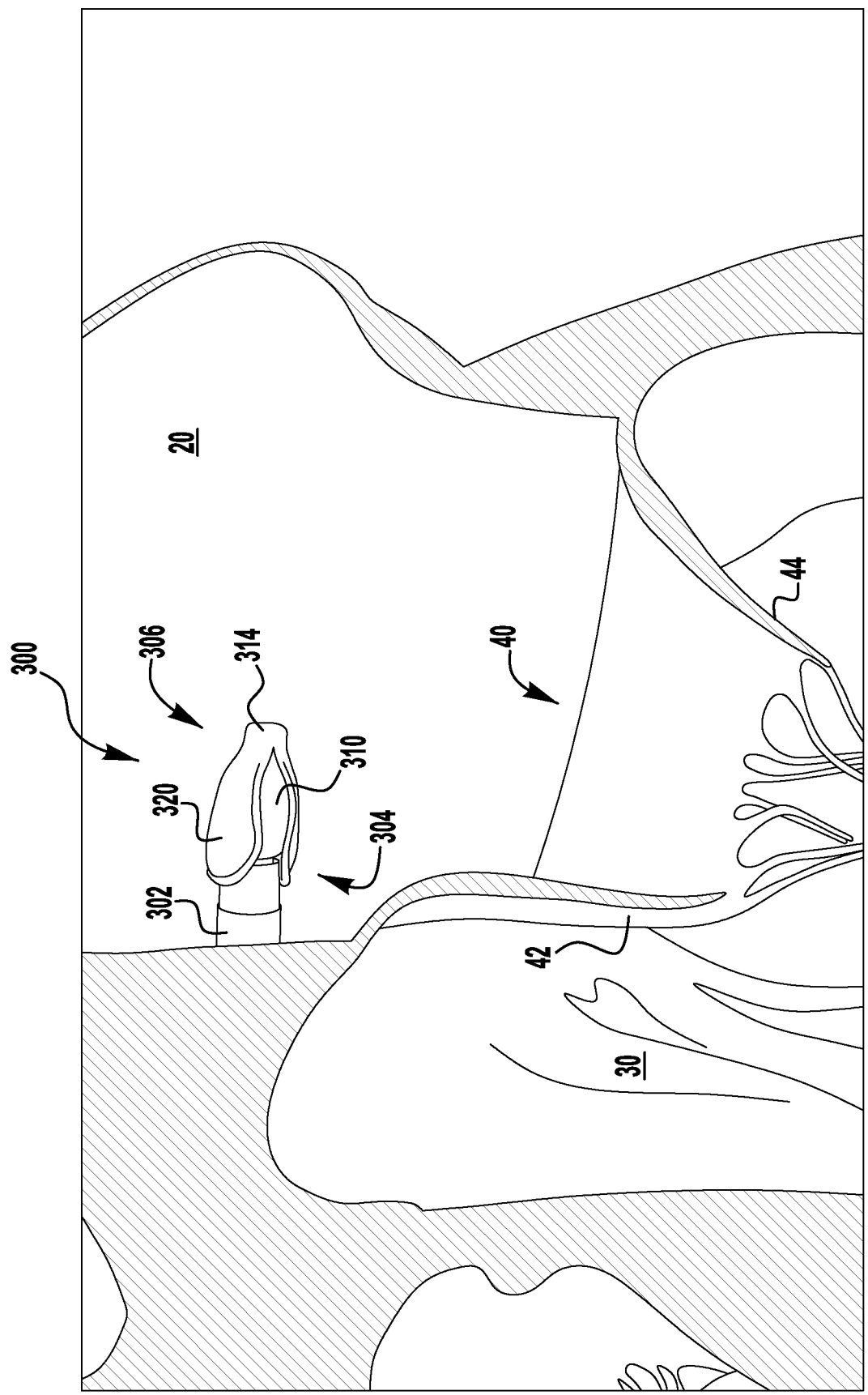
Figure 17:
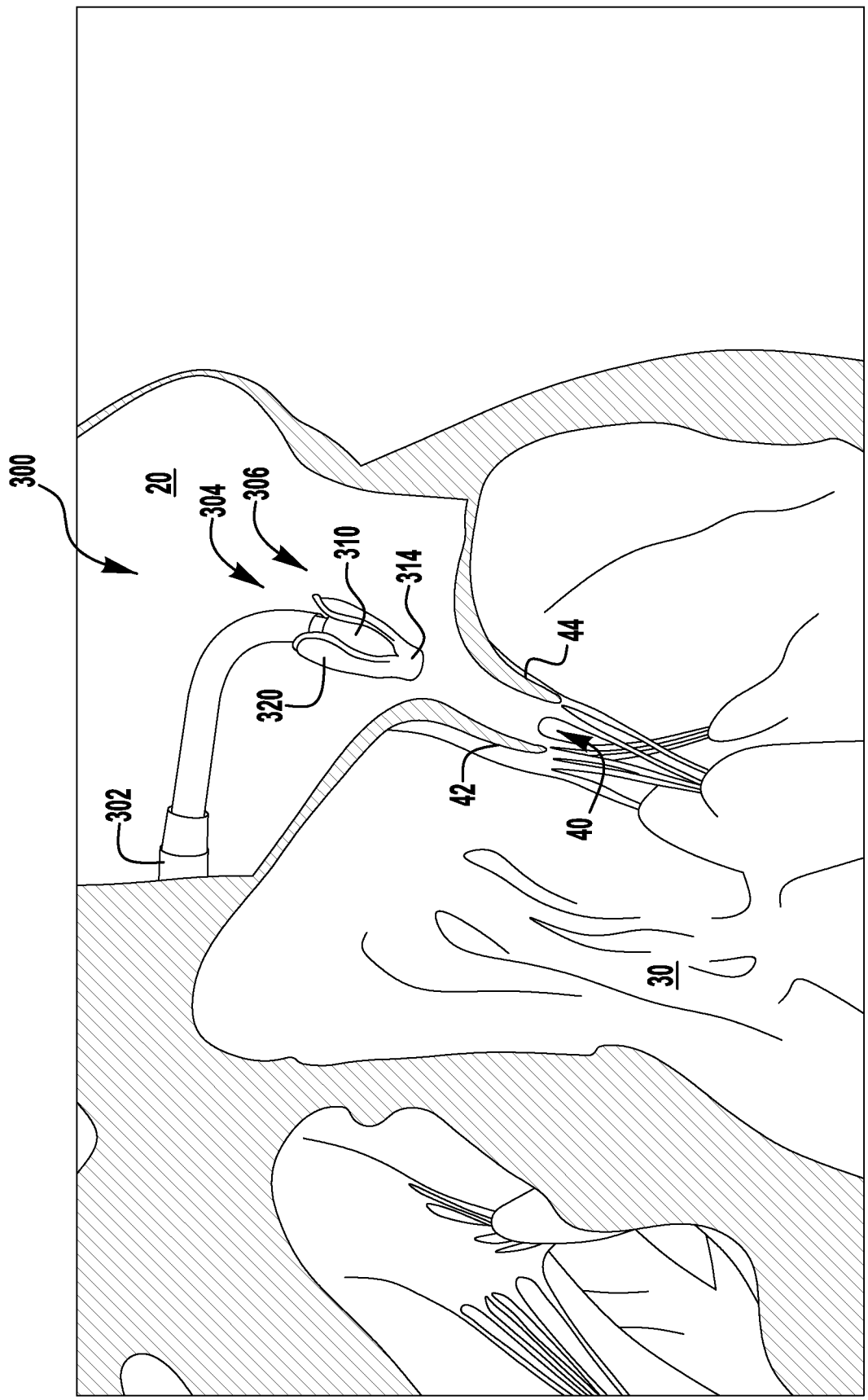
Figure 18:
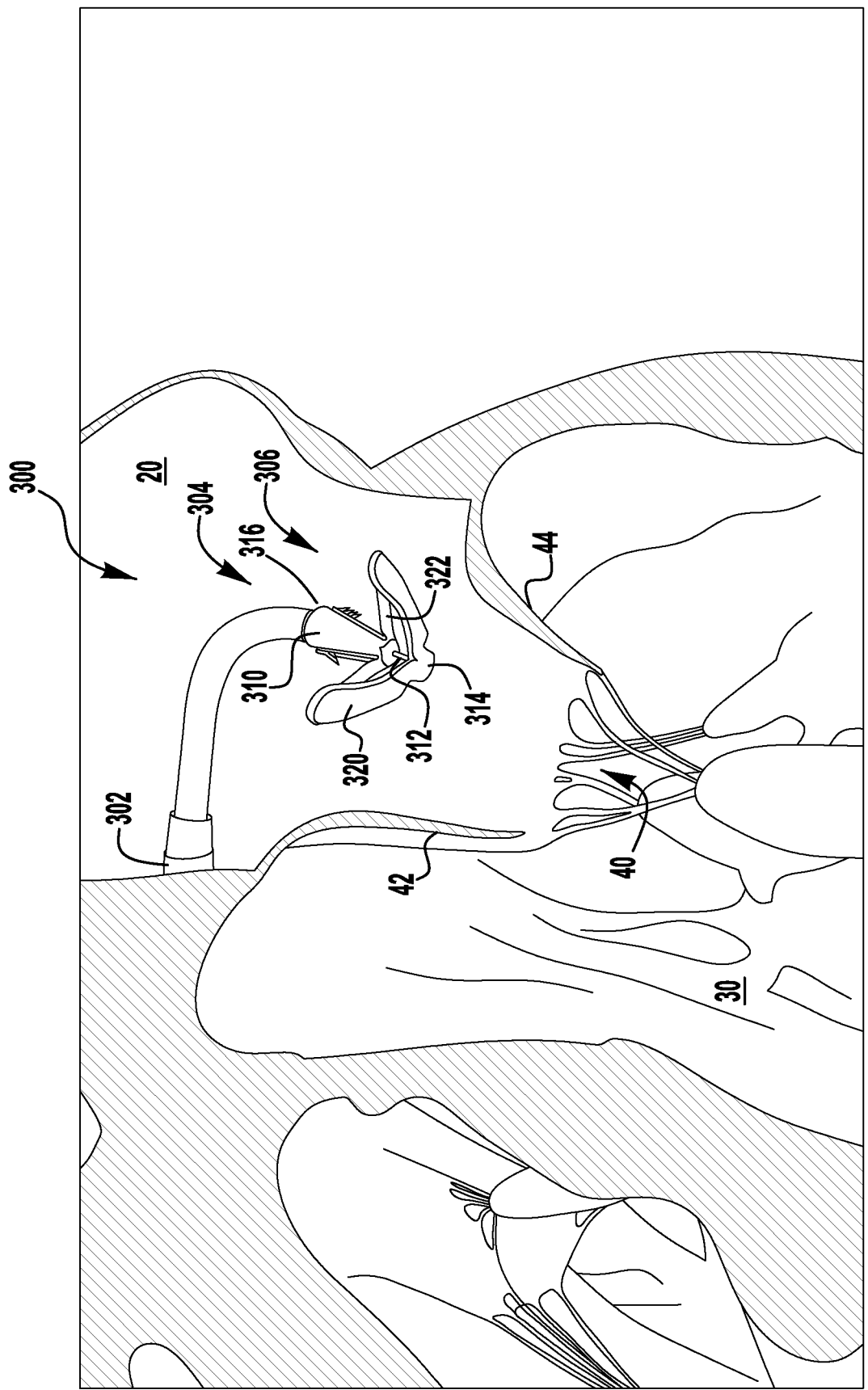
Figure 19:
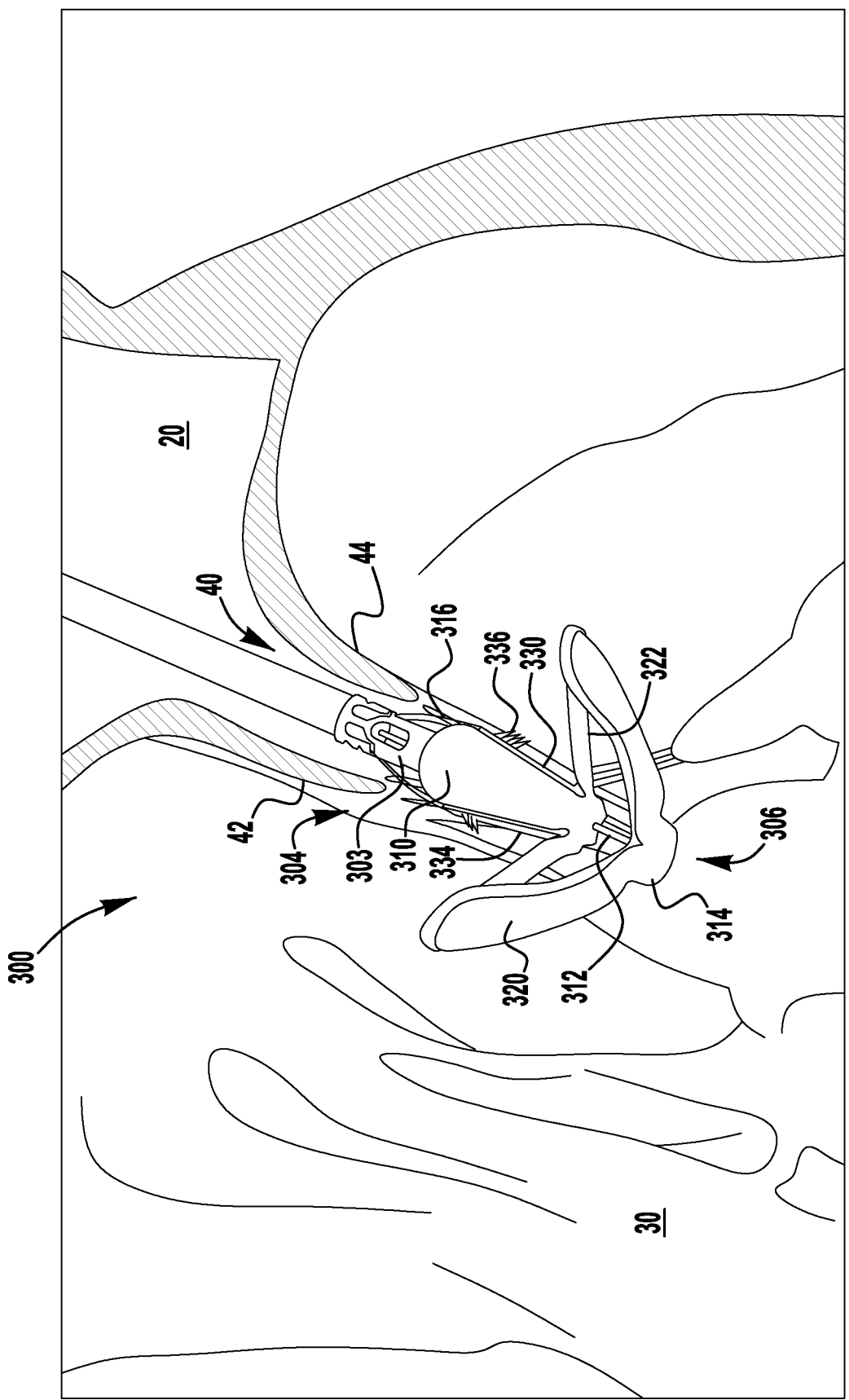
Figure 20:
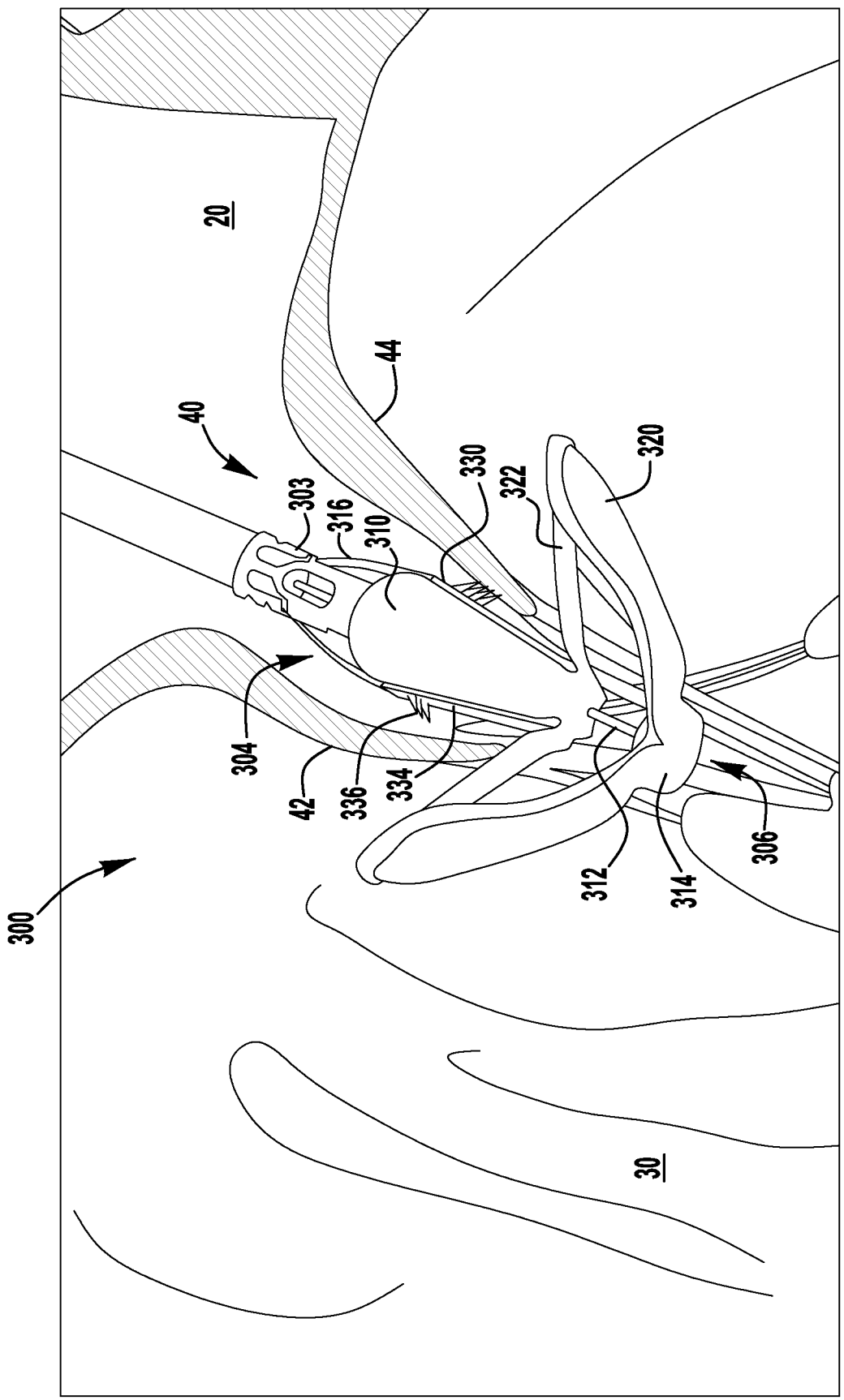
Figure 21:
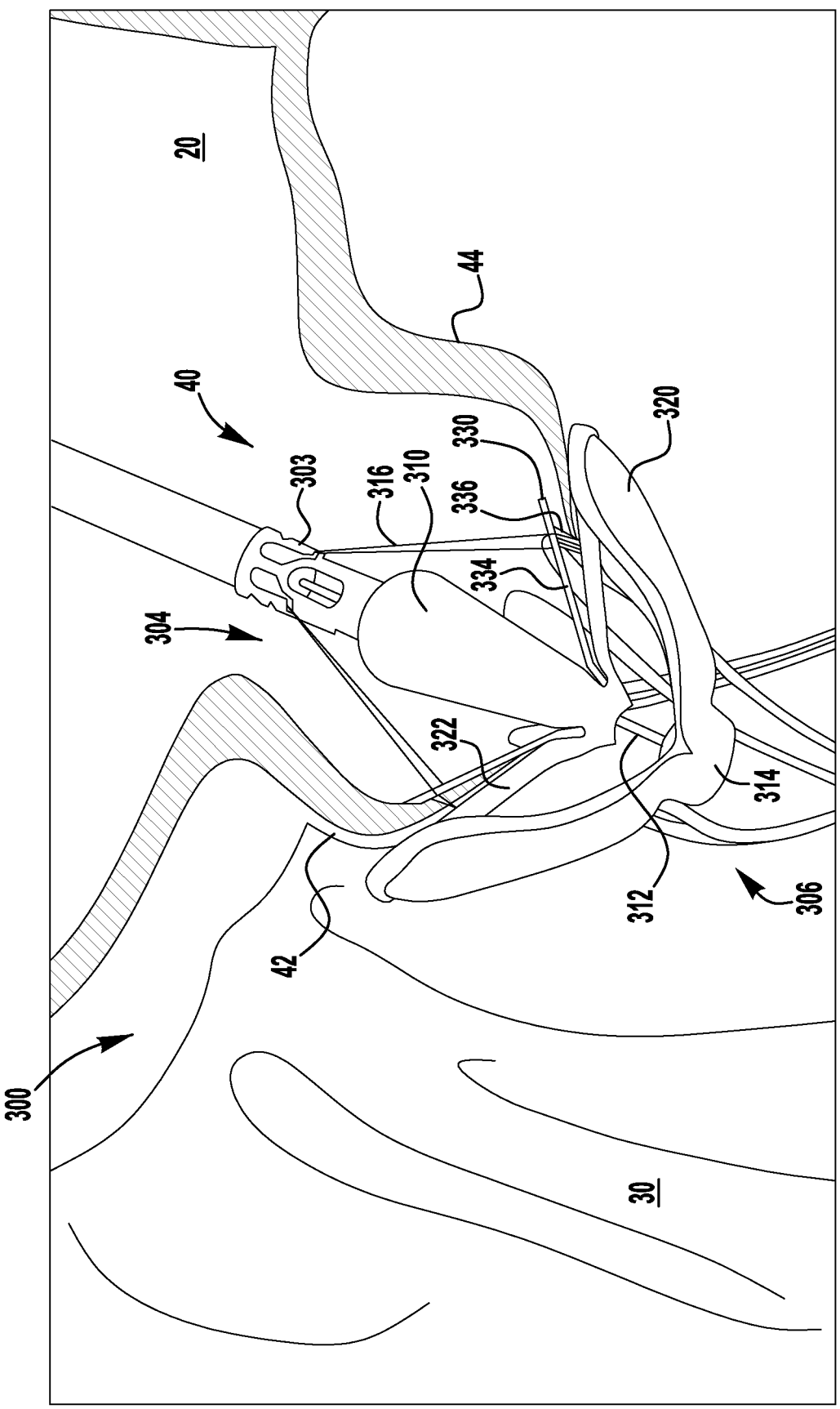
Figure 22:
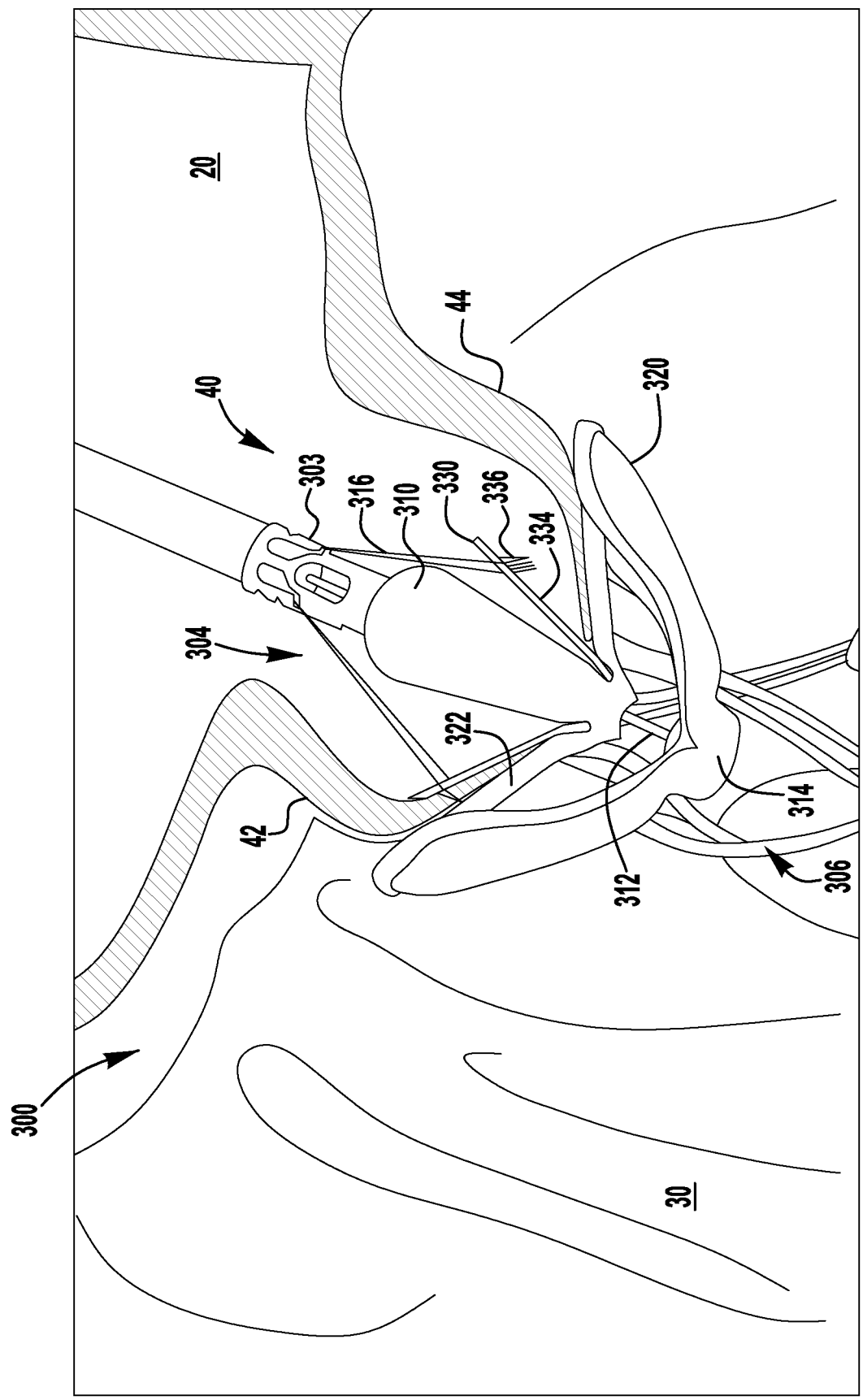
Figure 23:
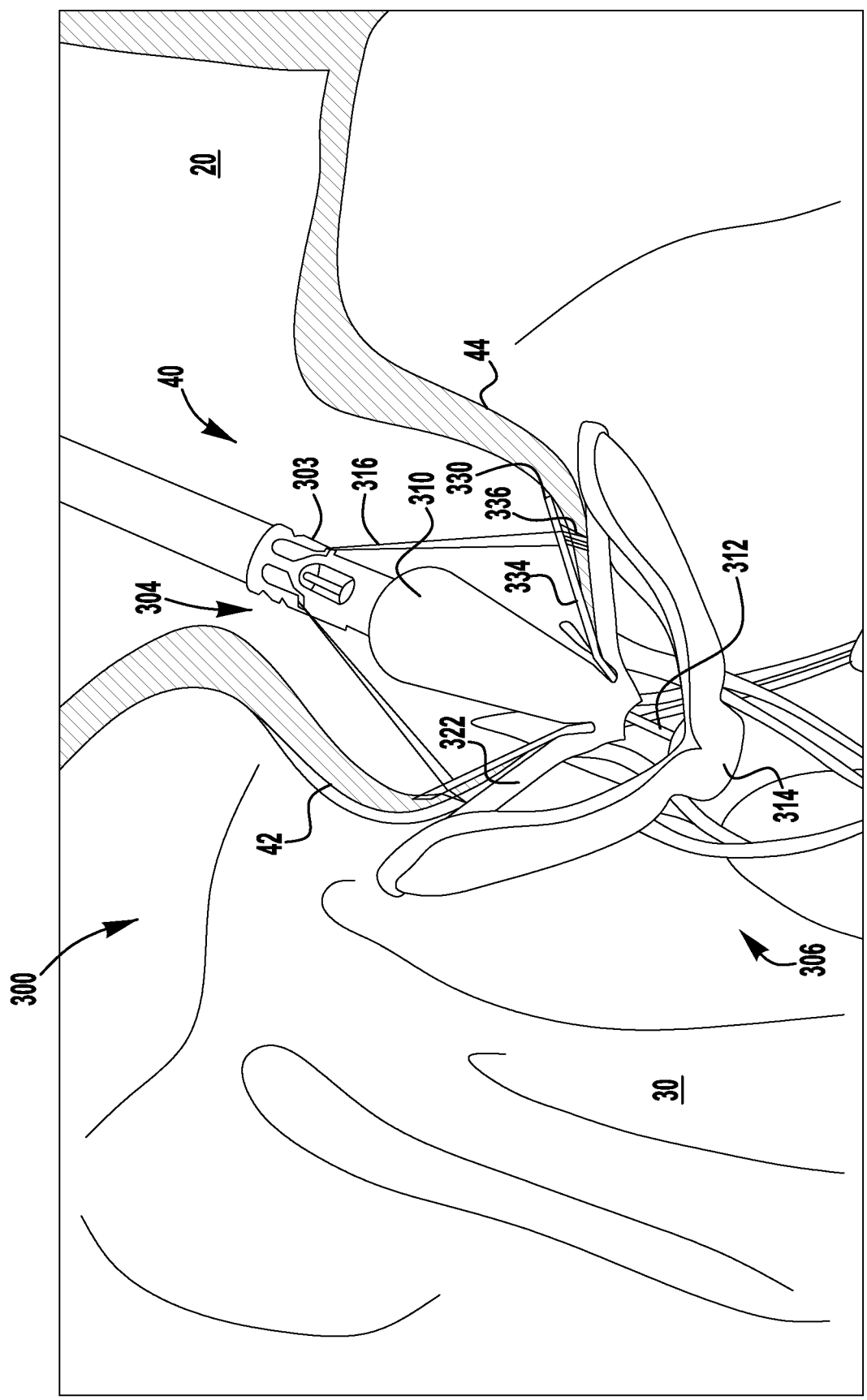
Figure 24:
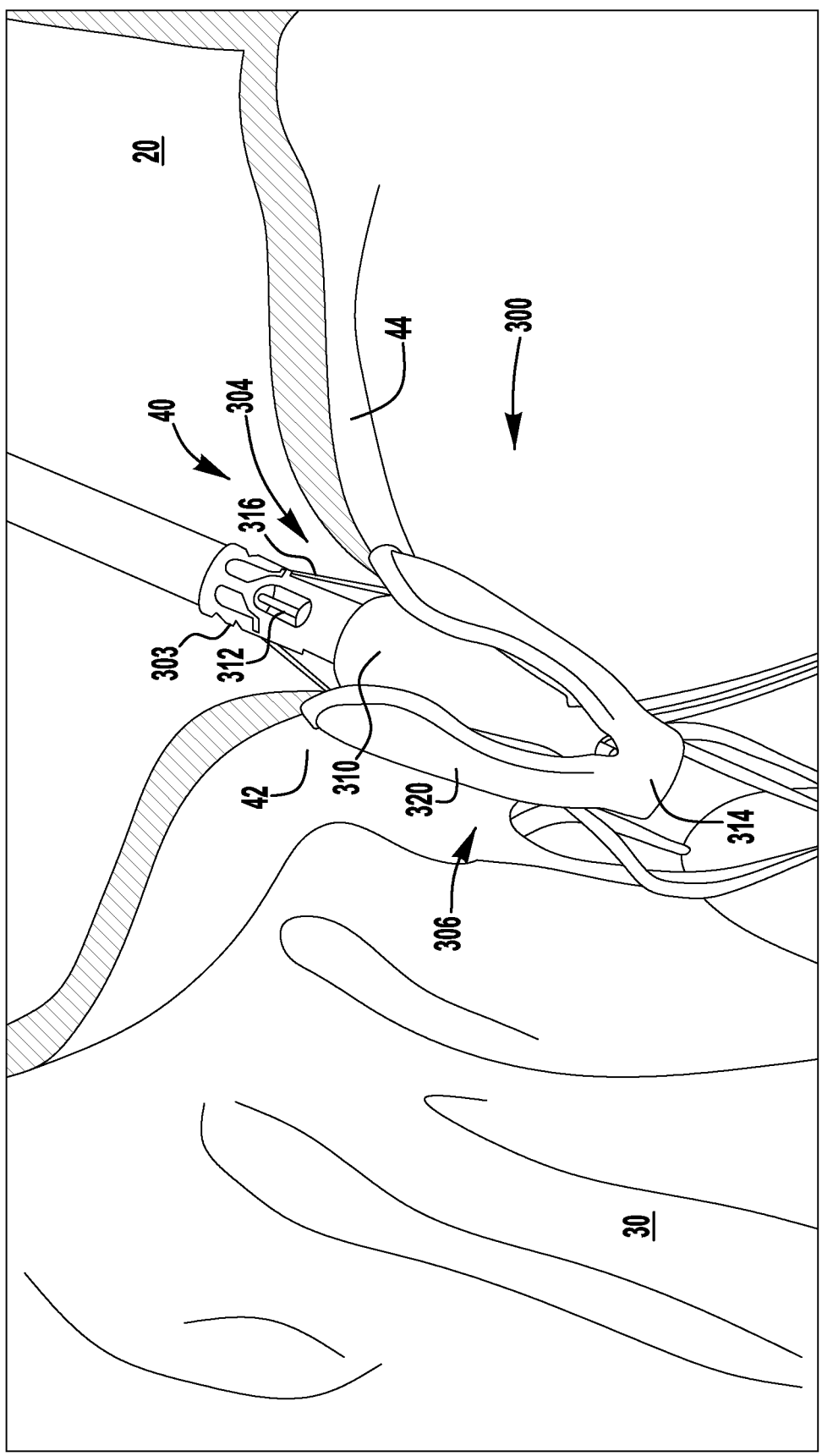
Figure 25:
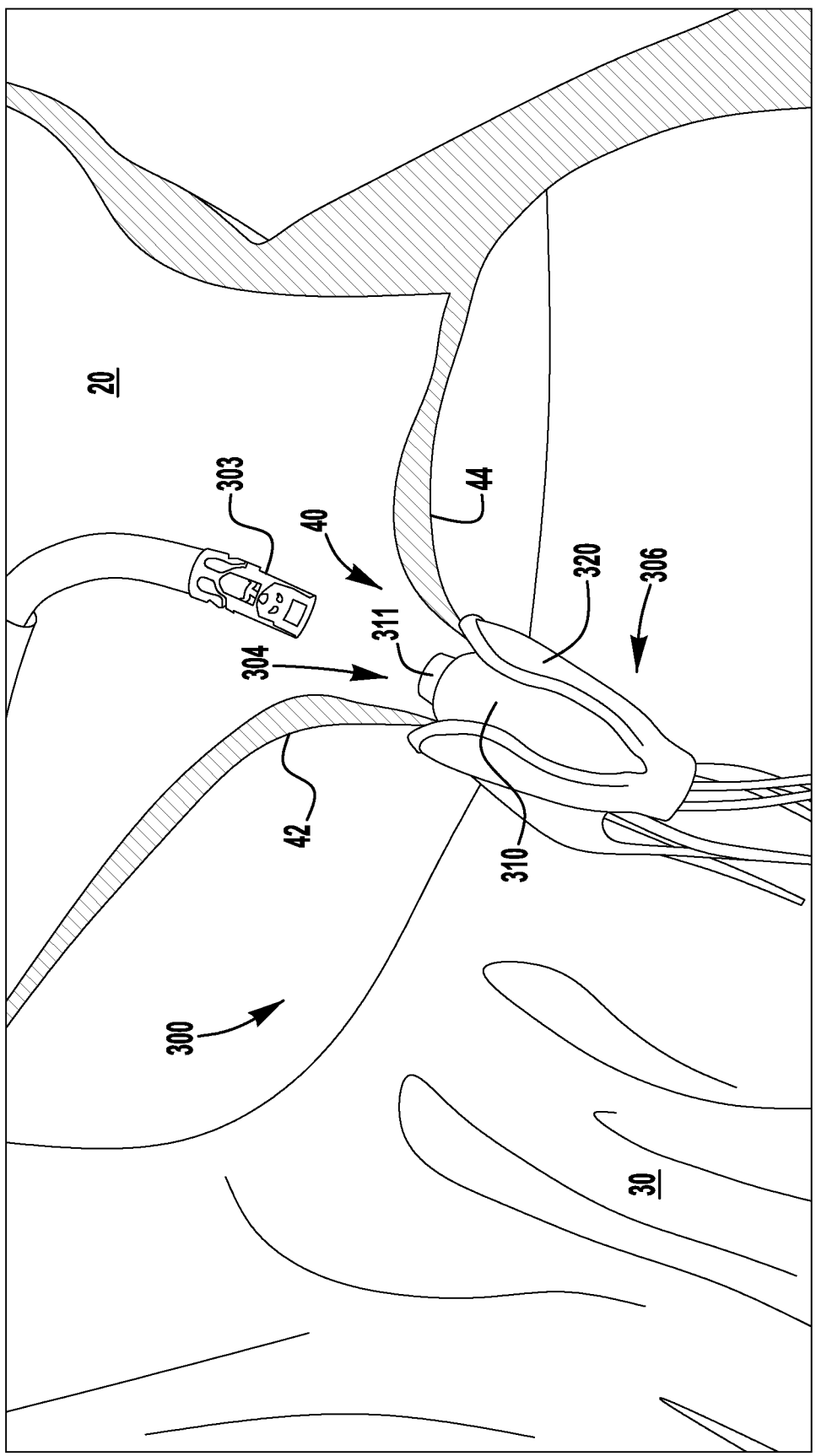

Referring now to FIG. 14, the delivery sheath is inserted into the left atrium 20 through the septum and the device 300 is deployed from the delivery sheath 302 in the fully open condition. The actuation wire 312 is then retracted to move the device 300 into the fully closed condition shown in FIGS. 15-16 and then maneuvered towards the mitral valve 40 as shown in FIG. 17. Referring now to FIG. 18, when the device 300 is aligned with the mitral valve 40, the actuation wire 312 is extended to open the paddles 320, 322 into the partially opened position and the actuation lines 316 are retracted to open the barbed clasps 330 to prepare for leaflet capture. Next, as shown in FIGS. 19-20, the partially open device 300 is inserted through the mitral valve 40 until leaflets are properly positioned in between the inner paddles 322 and the spacer 310 and inside the open barbed clasps 330. FIG. 21 shows the device 300 with both clasps 330 closed, though the barbs 336 of one clasp 330 missed one of the leaflets 44. As can be seen in FIGS. 22-23, the out of position clasp 330 is opened and closed again to properly capture the missed leaflet 44. When both leaflets 42, 44 are captured properly, the actuation wire 312 is retracted to move the device 300 into the fully closed position shown in FIG. 24. With the device 300 fully implanted in the native mitral valve 40, the actuation wire 312 is withdrawn to release the collar 303 from an upper end or plate 311 of the spacer 310. Once deployed, the device 300 may be maintained in the fully closed position with a mechanical means such as a latch, or may be biased to remain closed through the use of spring material, such as steel, and/or shape-memory alloys such as Nitinol. For example, the paddles 320, 322 may be formed of steel or Nitinol shape-memory alloy—produced in a wire, sheet, tubing, or laser sintered powder—and are biased to hold the outer paddles 320 closed around the spacer 310 and the barbed clasps 330 pinched around native leaflets.

Figure 26:
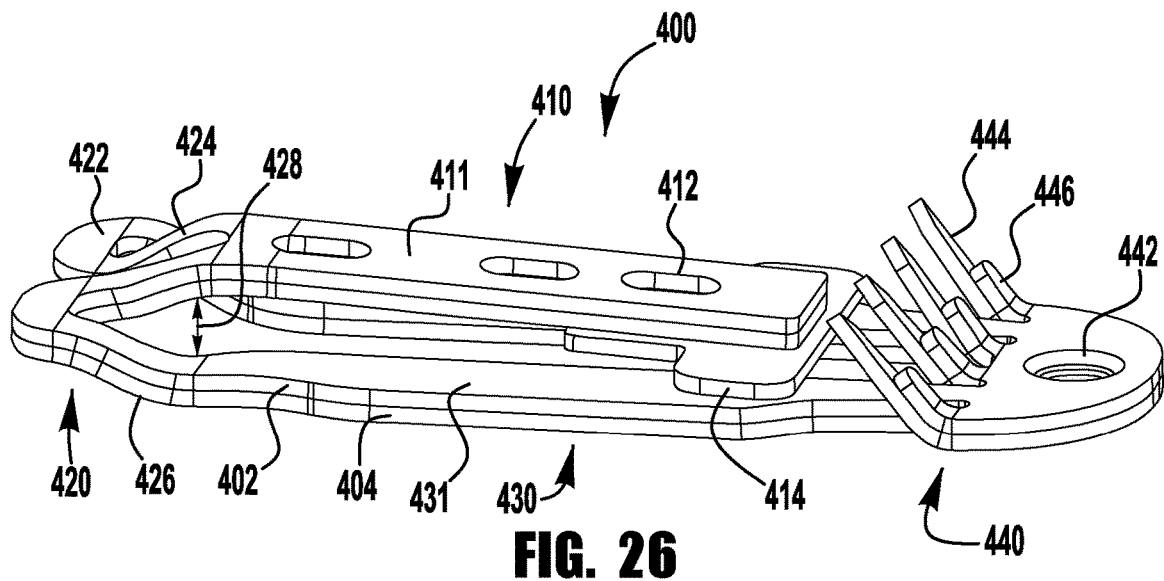
FIG. 26 shows a barbed clasp for an implantable prosthetic device according to one embodiment.

Referring now to FIG. 26, an exemplary barbed clasp 400 for use in implantable prosthetic devices, such as devices 100, 200, 300 described above, is shown. The barbed clasp 400 is formed from a top layer 402 and a bottom layer 404. The two-layer design of the clasp 400 allows thinner sheets of material to be used, thereby improving the flexibility of the clasp 400 over a clasp formed from a single thicker sheet, while maintaining the strength of the clasp 400 needed to successfully retain a native valve leaflet.

The barbed clasp 400 includes a fixed arm 410, a hinged portion 420, and a movable arm 430 having a barbed portion 440. The top and bottom layers 402, 404 have a similar shape and in certain embodiments are attached to each other at the barbed end 440. The hinged portion 420 is spring-loaded so that the fixed and moveable arms 410, 430 are biased toward each other when the barbed clasp 400 is in a closed condition. When assembled to an implantable prosthetic device, the fixed arm 410 is attached to a portion of the prosthetic device. The clasp 400 is opened by pulling on an actuation line attached to the moveable arm 430 until the spring force of the hinge portion 420 is overcome.

The fixed arm 410 is formed from a tongue 411 of material extending from the hinged portion 420 between two side beams 431 of the moveable arm 430. The tongue 411 is biased between the side beams 431 by the hinge portion 420 such that force must be applied to move the tongue 411 from a neutral position located beyond the side beams 431 to a preloaded position substantially parallel with the side beams 431. The tongue 411 is held in the preloaded position by a T-shaped cross-bar 414 that is attached to the tongue 411 and extends outward to engage the side beams 431. In certain embodiments, the angle between the fixed and moveable arms 410, 430 when the tongue is in the neutral position is about 30 to about 100 degrees, 30 to about 90 degrees, or about 30 to about 60 degrees, or about 40 to about 50 degrees, or about 45 degrees.

The tongue 411 includes holes 412 for receiving sutures (not shown) that attach the fixed arm 410 to an implantable device. In certain embodiments, the holes 412 are elongated slots or oval-shaped holes to accommodate sliding of the layers 402, 404 without damaging the sutures attaching the clasp 400 to an implantable device.

The hinge portion 420 is formed by two beam loops 422 that extend from the tongue 411 of the fixed arm 410 to the side beams 431 of the moveable arm 430. In certain embodiments, the beam loops 422 are narrower than the tongue 411 and side beam 431 to provide additional flexibility. The beam loops 422 each include a center portion 424 extending from the tongue 411 and an outer portion 426 extending to the side beams 431. The beam loops 422 are bent into a somewhat spiral or helical shape by bending the center and outer portions 424, 426 in opposite directions, thereby forming an offset or step distance 428 between the tongue 411 and side beams 431. The step distance 428 provides space between the arms 410, 430 to accommodate the native leaflet of the mitral valve after it is captured. In certain embodiments, the step distance 428 is about 0.5 millimeter to about 1 millimeters, or about 0.75 millimeters.

When viewed in a top plan view, the beam loops have an "omega-like" shape. This shape of the beam loops 422 allows the fixed and moveable arms 410, 430 to move considerably relative to each other without plastically deforming the clasp material. For example, in certain embodiments, the tongue 411 can be pivoted from a neutral position that is approximately 45 degrees beyond the moveable arm 430 to a fully open position that is approximately 180 degrees from the moveable arm 430 without plastically deforming the clasp material. In certain embodiments, the clasp material plastically deforms during opening without reducing or without substantially reducing the pinch force exerted between the fixed and moveable arms in the closed position.

Preloading the tongue 411 enables the clasp 400 to maintain a pinching or clipping force on the native leaflet when closed while also being able to be opened wide to more easily capture the native leaflet. The preloading of the tongue 411 provides a significant advantage over prior art clips that provide little or no pinching force when closed. Additionally, closing the clasp 400 with spring force is a significant improvement over clips that use a one-time locking closure mechanism, as the clasp 400 can be repeatedly opened and closed for repositioning on the leaflet while still maintaining sufficient pinching force when closed.

The barbed portion 440 of the moveable arm 430 includes an eyelet 442, barbs 444, and barb supports 446. Positioning the barbed portion of the clasp 400 at an end of the moveable arm 430 increases the space between the barbs 444 and the fixed arm 410 when the clasp 400 is opened, thereby improving the ability of the clasp 400 to successfully capture a leaflet during implantation. This distance also allows the barbs 444 to more reliably disengage from the leaflet for repositioning. In certain embodiments, the barbs of the clasps may be staggered longitudinally to further distribute pinch forces and local leaflet stress.

The barbs 444 are laterally spaced apart at the same distance from the hinge portion 420, providing a superior distribution of pinching forces on the leaflet tissue while also making the clasp more robust to leaflet capture than barbs arranged in a longitudinal row. In some embodiments, the barbs 444 can be staggered to further distribute pinch forces and local leaflet stress.

The barbs 442 are formed from the bottom layer 404 and the barb supports 446 are formed from the top layer. In certain embodiments, the barbs are formed from the top layer 402 and the barb supports are formed from the bottom layer 404. Forming the barbs 444 only in one of the two layers 402, 404 allows the barbs to be thinner and therefore effectively sharper than a barb formed from the same material that is twice as thick. The barb supports 446 extend along a lower portion of the barbs 444 to stiffen the barbs 444, further improving penetration and retention of the leaflet tissue. In certain embodiments, the ends of the barbs 444 are further sharpened using any suitable sharpening means.

The barbs 444 are angled away from the moveable arm 430 such that they easily penetrate tissue of the native leaflets with minimal pinching or clipping force. The barbs 444 extend from the moveable arm at an angle of about 45 degrees to about 75 degrees, or about 45 degrees to about 60 degrees, or about 48 to about 56 degrees, or about 52 degrees. The angle of the barbs 444 provides further benefits, in that force pulling the implant off of the native leaflet will encourage the barbs 444 to further engage the tissue, thereby ensuring better retention. Retention of the leaflet in the clasp 400 is further improved by the position of the T-shaped cross bar 414 near the barbs 444 when the clasp 400 is closed. In this arrangement, the tissue pierced by the barbs 444 is pinched against the moveable arm 430 at the cross bar 414 location, thereby forming the tissue into an S-shaped torturous path as it passes over the barbs 444. Thus, forces pulling the leaflet away from the clasp 400 will encourage the tissue to further engage the barbs 444 before the leaflets can escape.

Each layer 402, 404 of the clasp 400 is laser cut from a sheet of shape-memory alloy, such as Nitinol. The top layer 402 is aligned and attached to the bottom layer 404. In certain embodiments, the layers 402, 404 are attached at the barbed end 440 of the moveable arm 430. For example, the layers 402, 404 may be attached only at the barbed end 440, to allow the remainder of the layers to slide relative to one another. Portions of the combined layers 402, 404, such as a fixed arm 410, barbs 444 and barb supports 446, and beam loops 422 are bent into a desired position. The clasp 400 is then subjected to a shape-setting process so that internal forces of the material will tend to return to the set shape after being subjected to deformation by external forces. After shape setting, the tongue 411 is moved to its preloaded position so that the cross-bar 414 can be attached. Consequently, the clasp 400 can be completely flattened for delivery through a delivery sheath and allowed to expand once deployed within the heart.

The clasp 400 is opened and closed by applying and releasing tension on a suture (not shown) attached to the moveable arm 430. The suture is inserted through an eyelet 442 near the barbed portion 440 of the moveable arm 430 and wraps around the end of the moveable arm 430 before returning to the delivery sheath. In certain embodiments, an intermediate suture loop is made through the eyelet and the suture is inserted through the intermediate loop. An intermediate loop of suture material reduces friction experienced by the actuation suture relative to the friction between the actuation suture and the clasp material. When the suture is looped through the eyelet 442 or intermediate loop, both ends of the actuation suture extend back into and through the delivery sheath 102 (see FIG. 1). The suture can be removed by pulling one end of the suture proximally until the other end of the suture pulls through the eyelet or intermediate loop and back into the delivery sheath.

Figure 27:
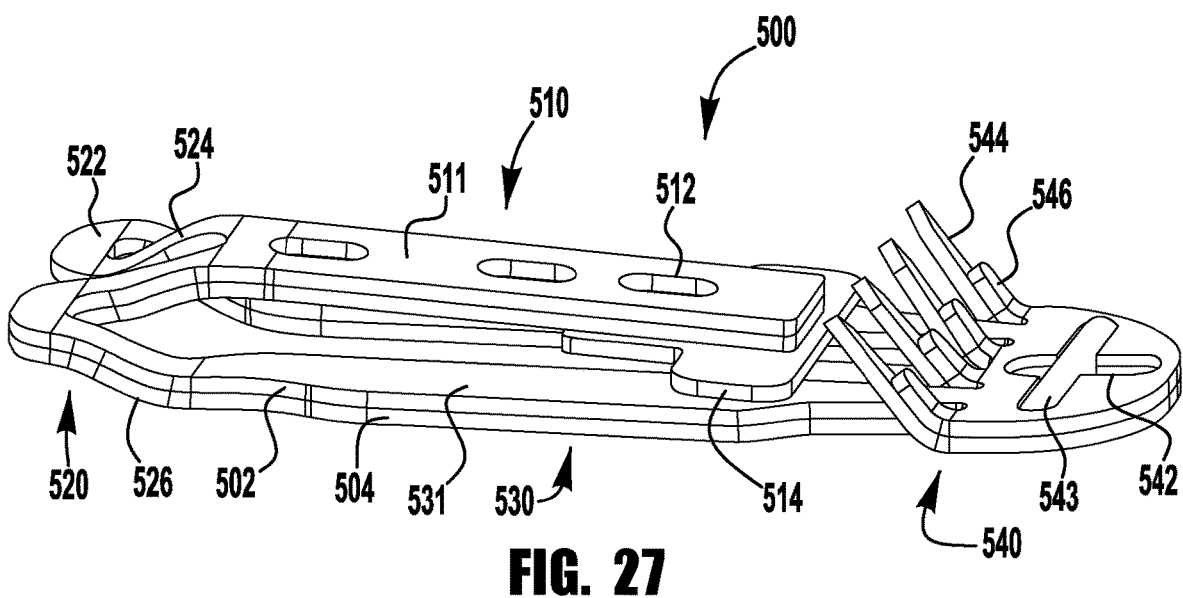
FIG. 27 shows a barbed clasp for an implantable prosthetic device according to a second embodiment.

Referring now to FIG. 27, an exemplary barbed clasp 500 for use in implantable prosthetic devices, such as devices 100, 200, 300 described above, is shown. The barbed clasp 500 is substantially the same as the barbed clasp 400, except the barbed clasp 500 includes a suture pin 543 disposed across an opening 542, instead of the hole 442. The barbed clasp 500 is formed from a top layer 502 and a bottom layer 504. The two-layer design of the clasp 500 allows thinner sheets of material to be used, thereby improving the flexibility of the clasp 500 over a clasp formed from a single thicker sheet, while maintaining the strength of the clasp 500 needed to successfully retain a native valve leaflet.

The barbed clasp 500 includes a fixed arm 510, a hinged portion 520, and a movable arm 530 having a barbed portion 540. The top and bottom layers 502, 504 have a similar shape and in certain embodiments are attached to each other at the barbed end 540. The hinged portion 520 is spring-loaded so that the fixed and moveable arms 510, 530 are biased toward each other when in the barbed clasp 500 is in a closed condition. When assembled to an implantable prosthetic device, the fixed arm 510 is attached to a portion of the prosthetic device. The clasp 500 is opened by pulling on an actuation line attached to the moveable arm 530 until the spring force of the hinge portion 520 is overcome.

The fixed arm 510 is formed from a tongue 511 of material extending from the hinged portion 520 between two side beams 531 of the moveable arm 530. The tongue 511 is biased between the side beams 531 by the hinge portion 520 such that force must be applied to move the tongue 511 from a neutral position located beyond the side beams 531 to a preloaded position substantially parallel with the side beams 531. The tongue 511 is held in the preloaded position by a T-shaped cross-bar 514 that is attached to the tongue 511 and extends outward to engage the side beams 531. In certain embodiments, the angle between the fixed and moveable arms 510, 530 when the tongue is in the neutral position is about 30 to about 100 degrees, or about 30 to about 90 degrees, or about 30 to about 60 degrees, or about 40 to about 50 degrees, or about 45 degrees.

The tongue 511 includes holes 512 for receiving sutures (not shown) that attach the fixed arm 510 to an implantable device. In certain embodiments, the holes 512 are elongated slots or oval-shaped holes to accommodate sliding of the layers 502, 504 without damaging the sutures attaching the clasp 500 to an implantable device.

The hinge portion 520 is formed by two beam loops 522 that extend from the tongue 511 of the fixed arm 510 to the side beams 531 of the moveable arm 530. In certain embodiments, the beam loops 522 are narrower than the tongue 511 and side beam 531 to provide additional flexibility. The beam loops 522 each include a center portion 524 extending from the tongue 511 and an outer portion 526 extending to the side beams 531. The beam loops 522 are bent into a somewhat spiral or helical shape by bending the center and outer portions 524, 526 in opposite directions, thereby forming a step distance 528 between the tongue 511 and side beams 531. The step distance 528 provides space between the arms 510, 530 to accommodate the native leaflet of the mitral valve after it is captured. In certain embodiments, the step distance 528 is about 0.5 millimeter to about 1 millimeters, or about 0.75 millimeters.

When viewed in a top plan view, the beam loops have an "omega-like" shape. This shape of the beam loops 522 allows the fixed and moveable arms 510, 530 to move considerably relative to each other without plastically deforming the clasp material. For example, in certain embodiments, the tongue 511 can be pivoted from a neutral position that is approximately 45 degrees beyond the moveable arm 530 to a fully open position that is approximately 180 degrees from the moveable arm 530 without plastically deforming the clasp material. In certain embodiments, the clasp material plastically deforms during opening without reducing the pinch force exerted between the fixed and moveable arms in the closed position.

Preloading the tongue 511 enables the clasp 500 to maintain a pinching or clipping force on the native leaflet when closed while also being able to be opened wide to more easily capture the native leaflet. The preloading of the tongue 511 provides a significant advantage over prior art clips that provide little or no pinching force when closed. Additionally, closing the clasp 500 with spring force is a significant improvement over clips that use a one-time locking closure mechanism, as the clasp 500 can be repeatedly opened and closed for repositioning on the leaflet while still maintaining sufficient pinching force when closed.

The barbed portion 540 of the moveable arm 530 includes an eyelet 542, barbs 544, and barb supports 546. Positioning the barbed portion of the clasp 500 at an end of the moveable arm 530 increases the space between the barbs 544 and the fixed arm 510 when the clasp 500 is opened, thereby improving the ability of the clasp 500 to successfully capture a leaflet during implantation. This distance also allows the barbs 544 to more reliably disengage from the leaflet for repositioning. In certain embodiments, the barbs of the clasps may be staggered longitudinally to further distribute pinch forces and local leaflet stress.

The barbs 544 are laterally spaced apart at the same distance from the hinge portion 520, providing a superior distribution of pinching forces on the leaflet tissue while also making the clasp more robust to leaflet capture than barbs arranged in a longitudinal row.

The barbs 544 are formed from the bottom layer 504 and the barb supports 546 are formed from the top layer. Forming the barbs 544 only in one of the two layers 502, 504 allows the barbs to be thinner and therefore effectively sharper than a barb formed from the same material that is twice as thick. The barb supports 546 extend along a lower portion of the barbs 544 to stiffen the barbs 544, further improving penetration and retention of the leaflet tissue. In certain embodiments, the ends of the barbs 544 are further sharpened using any suitable sharpening means.

The barbs 544 are angled away from the moveable arm 530 such that they easily penetrate tissue of the native leaflets with minimal pinching or clipping force. The barbs 544 extend from the moveable arm at an angle of about 45 to about 75 degrees, or about 45 to about 60 degrees, or about 48 to about 56 degrees, or about 52 degrees. The angle of the barbs 544 provides further benefits, in that force pulling the implant off of the native leaflet will encourage the barbs 544 to further engage the tissue, thereby ensuring better retention. Retention of the leaflet in the clasp 500 is further improved by the position of the T-shaped cross bar 514 near the barbs 544 when the clasp 500 is closed. In this arrangement, the tissue pierced by the barbs 544 is pinched against the moveable arm 530 at the cross bar 514 location, thereby forming the tissue into an S-shaped torturous path as it passes over the barbs 544. Thus, forces pulling the leaflet away from the clasp 500 will encourage the tissue to further engage the barbs 544 before the leaflets can escape.

Each layer 502, 504 of the clasp 500 is laser cut from a sheet of shape-memory alloy, such as Nitinol. The top layer 502 is aligned and attached to the bottom layer 504. In certain embodiments, the layers 502, 504 are attached at the barbed end 540 of the moveable arm 530. For example, the layers 402, 404 may be attached only at the barbed end 440, to allow the remainder of the layers to slide relative to one another. Portions of the combined layers 502, 504, such as a fixed arm 510, barbs 544 and barb supports 546, and beam loops 522 are bent into a desired position. The clasp 500 is then subjected to a shape-setting process so that internal forces of the material will tend to return to the set shape after being subjected to deformation by external forces. After shape setting, the tongue 511 is moved to its preloaded position so that the cross-bar 514 can be attached. Consequently, the clasp 500 can be completely flattened for delivery through a delivery sheath and allowed to expand once deployed within the heart.

The clasp 500 is opened and closed by applying and releasing tension on a suture (not shown) attached to the moveable arm 530. The suture is inserted through an opening 542 in the moveable arm 530 and looped around a pin 543 disposed in the opening 542. The smooth round shape of the pin 543 allows tension to be applied to the moveable arm 530 from many directions without causing the suture to wear. In certain embodiments, an intermediate suture loop is made through the opening and around the pin and the suture is inserted through the intermediate loop. An intermediate loop of suture material reduces friction experienced by the actuation suture relative to the friction between the actuation suture and the clasp material. When the actuation suture is looped around the pin 543, both ends of the suture extend back into and through the delivery sheath 102 (see FIG. 1). The suture can be removed by pulling one end of the suture proximally, until the other end of the suture pulls around the pin 543 and back into the delivery sheath.

Referring now to FIGS. 28-31, an exemplary barbed clasp 600 similar to barbed clasps 400 and 500 is shown in a variety of bent positions to illustrate the independent movement of the layers forming the barb clasps 400, 500, and 600. The barbed clasp 600 is formed from a top layer 602 and a bottom layer 604. The barbed clasp 600 includes a moveable arm 620, a fixed arm 622, a hinge portion 624. The moveable arm 620 includes a barbed portion 626 with barbs 628. The barbed clasp 600 does not include a cross-bar to prevent the moveable arm 620 from moving past the fixed arm 622. Instead of a cross-bar, the moveable arm 620 is held in a closed position with the fixed arm 622 by the inner paddle (not shown). To better illustrate the preloading of the clasp 600, FIGS. 28-31 show the fixed arm 622 moving relative to a stationary moveable arm 620. When assembled to an implantable device, however, the moveable arm 620 would move relative to the fixed arm 622 that is attached to the device.

Figure 28:
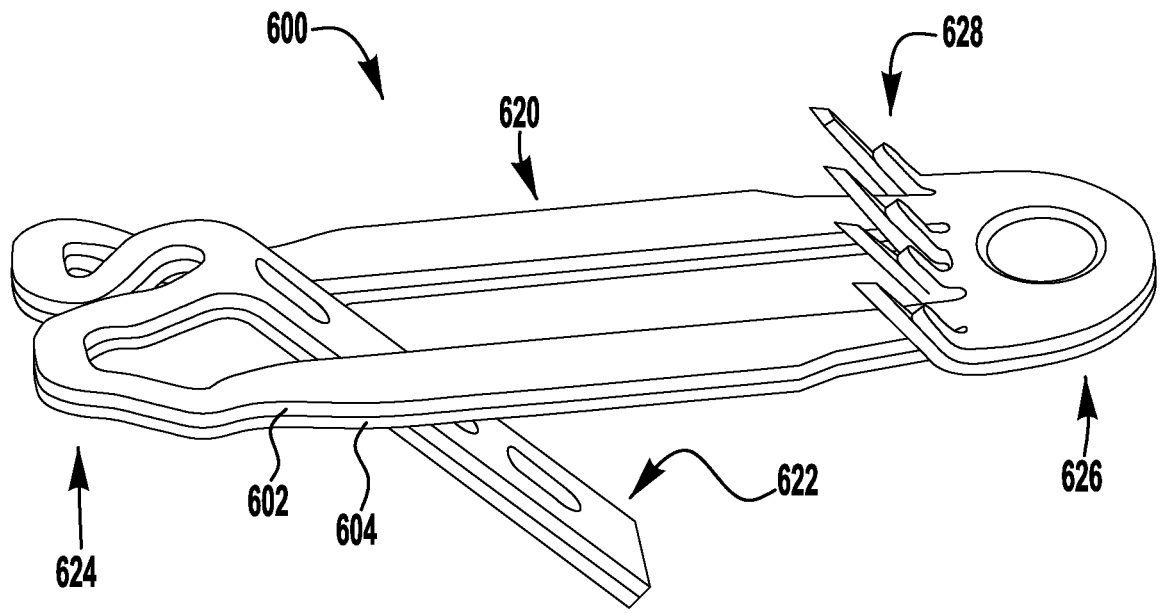
FIG. 28 shows a barbed clasp for an implantable prosthetic device according to a third embodiment.
Figure 29:
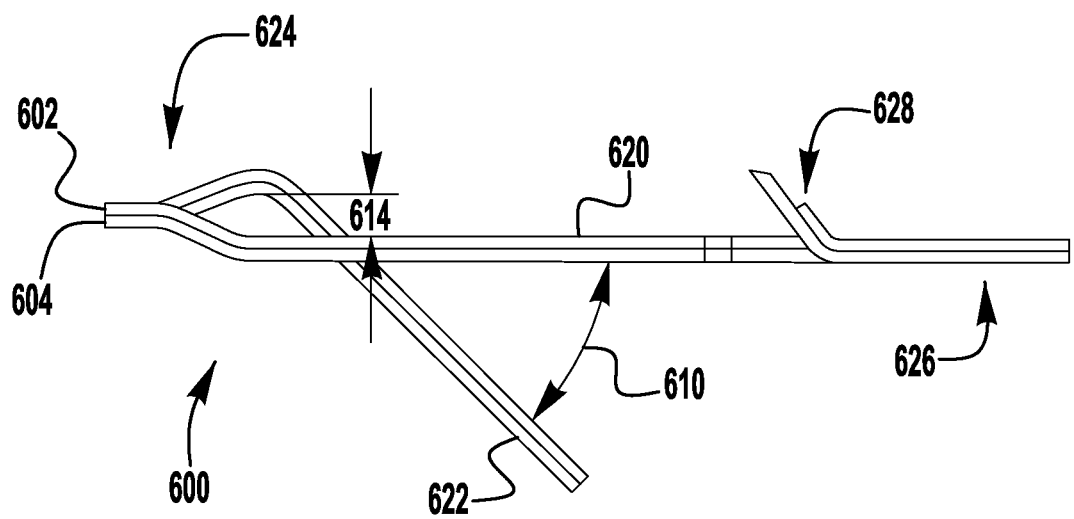
FIGS. 29-31 show a side view of barbed clasp for an implantable prosthetic device in various stages of bending.

Referring now to FIGS. 28-29, the clasp 600 is shown in a preloading or shape setting condition. The fixed arm 622 is bent below the moveable arm 620 by an angle 610 before the shape setting operation is performed. Force must be applied then to return the fixed arm 622 to a parallel relationship with the moveable arm 620. Thus, increasing the preloading angle 610 increases the force required to move the fixed arm 622, thereby increasing the preloading spring force pinching the arms 620, 622 together when the clasp 600 is closed. In other words, the greater the angle 610, the greater the spring force applied to captured tissue by the arms 620, 622.

Figure 30:
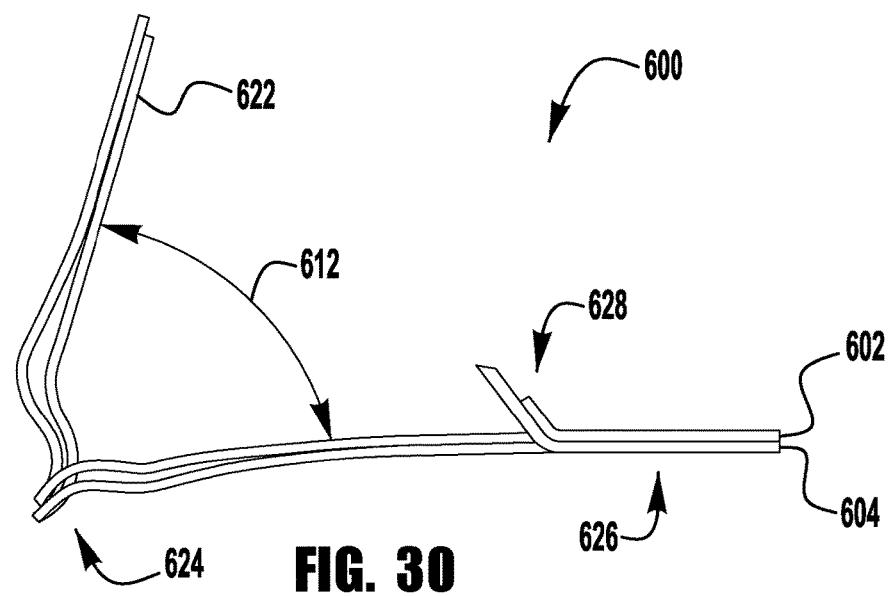
Figure 31:
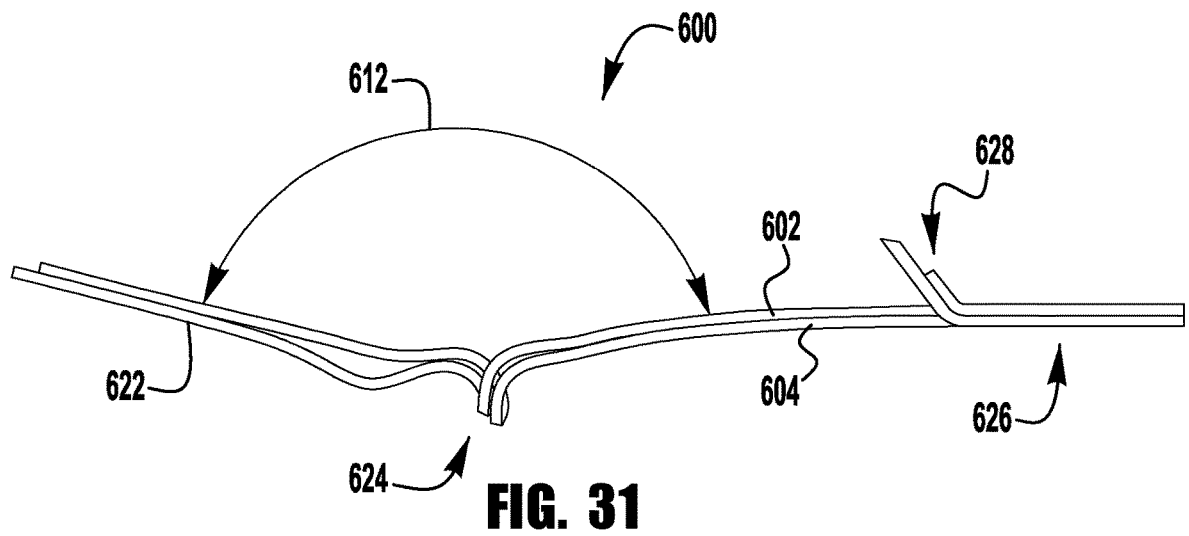

Referring now to FIGS. 30-31, the clasp 600 is shown being opened to an opening angle 612. As can be seen in FIGS. 30 and 31, the beam loops of the hinge portion 624 tend to separate as the clasp 600 is opened. Allowing the layers 602, 604 to separate during bending decreases strain on the material, thereby further increasing the maximum opening angle 612 that can be achieved before plastic deformation of the clasp material. As noted above, the hinge portion 624 is shaped to form somewhat spiral or helical beam loops, thereby forming a gap or step distance 614 between the arms 620, 622 (FIG. 29) that allows the leaflet tissue to be captured.

As the clasp 600 is opened, the layers 602, 604 in the fixed arm 622 slide relative to each other. In some embodiments, holes through the fixed 622 arm are elongated so that sutures securing the fixed arm 622 to the implantable device are not pinched by the sliding movement of the layers, nor are the layers 602, 604 constrained from sliding, which reduces strain experienced by the clasp material.

Referring now to FIGS. 32-35, exemplary barb clasps 700, 800, 900, and 1000 are shown. Barb clasps 700, 800, 900, and 1000, like clasps 400, 500, 600 can be used in the implantable devices 100, 200, and 300 described above. Unlike barbed clasps 400, 500, 600, however, barbed clasps 700, 800, 900, and 1000 are formed by laser cutting material from the side of the clasp rather than from the top. Laser cutting from the side reduces the operations required to manufacture the clasp and allows the thickness of the clasp to be varied to vary the bending properties of portions of the clasp based on the function of each portion. For example, hinge portions may be thinner to provide more flexibility while arms may be thickened to provide more stiffness.

Figure 32:
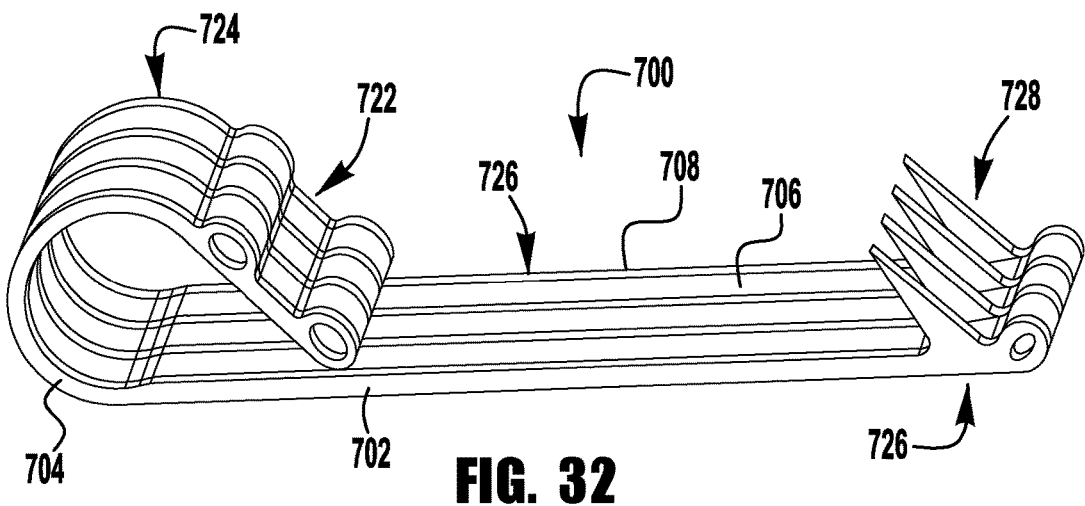
FIG. 32 shows a barbed clasp for an implantable prosthetic device according to a fourth embodiment.

Referring now to FIG. 32, a laminated barb clasp 700 is shown. The barb clasp 700 has thick and thin portions 702, 704 and is formed from alternating spacer layers 706 and barbed layers 708 to form a laminated structure. The clasp 700 includes a moveable arm 720, a fixed arm 722, and a hinge portion 724. The moveable arm 720 includes a barbed portion 726 having barbs 728 formed in the barbed layers 708. Forming the layers 706, 708 by laser cutting from a side profile allows the barbs 728 to be tapered, thereby providing a stiff barb with a sharp point. The fixed arm 722 includes holes to secure the clasp 700 to an implantable device. When assembled to an implantable device, the fixed arm 722 is extended by the attached inner paddle, thus the native tissue is pinched between the moveable arm 720 and the inner paddle of the device.

Figure 33:
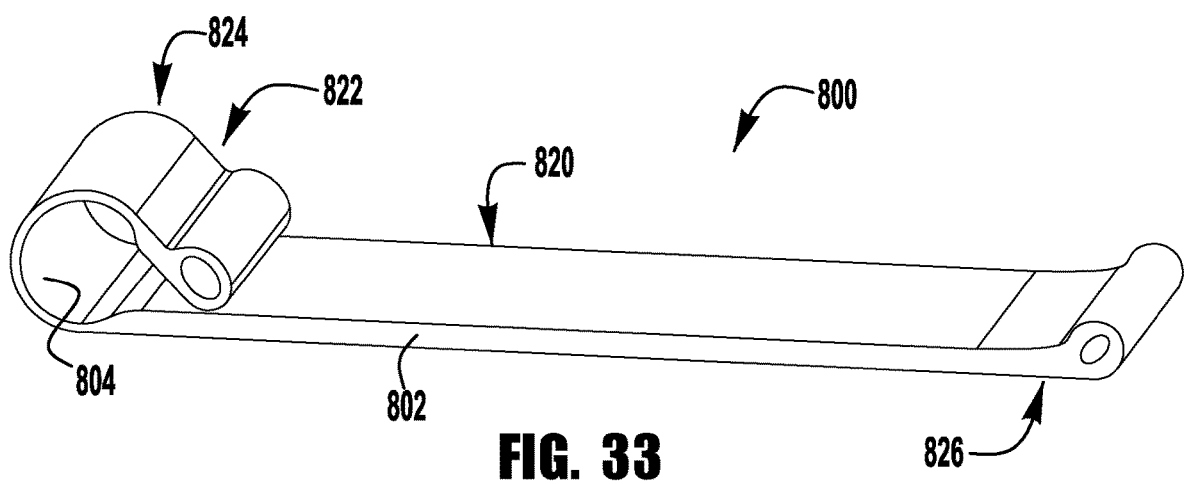
FIG. 33 shows a barbed clasp for an implantable prosthetic device according to a fifth embodiment.
Figure 34:
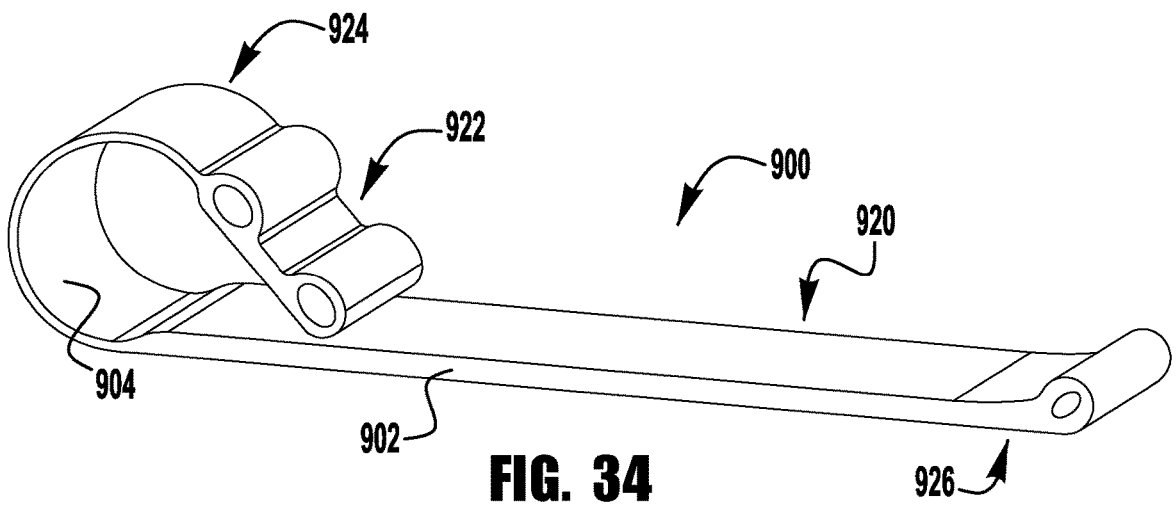
FIG. 34 shows a barbed clasp for an implantable prosthetic device according to a sixth embodiment.
Figure 35:
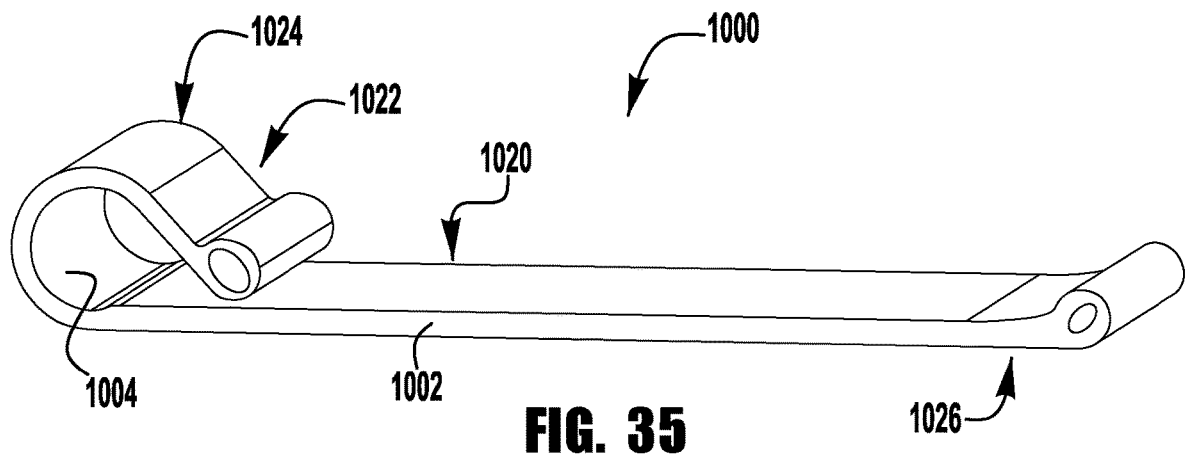
FIG. 35 shows a barbed clasp for an implantable prosthetic device according to a seventh embodiment.

Referring now to FIGS. 33-35, exemplary barb clasps 800, 900, 1000 are shown. The clasps 800, 900, 1000 are similar in overall shape while illustrating the variety of thicknesses possible when laser cutting clasps from the side. The clasps 800, 900, 1000 have a thin portion 804, 904, 1004 and a thick portion 802, 902, 1002. The clasps 800, 900, 1000 include a moveable arm 820, 920, 1020, a fixed arm 822, 922, 1022, a hinge portion 824, 924, 1024. The moveable arm 820, 920, 1020 includes a barb portion 826, 926, 1026 having barbs (not shown) similar to the barbs 726 of clasp 700. As can be seen in FIGS. 33-35, holes can be provided in the fixed arm 822, 922, 1022 to secure the clasp 800, 900, 1000 to an implantable device. When assembled to an implantable device, the fixed arm 822, 922, 1022 is extended by the attached inner paddle, thus the native tissue is pinched between the moveable arm 820, 920, 1020 and the inner paddle of the device.

Figure 36:
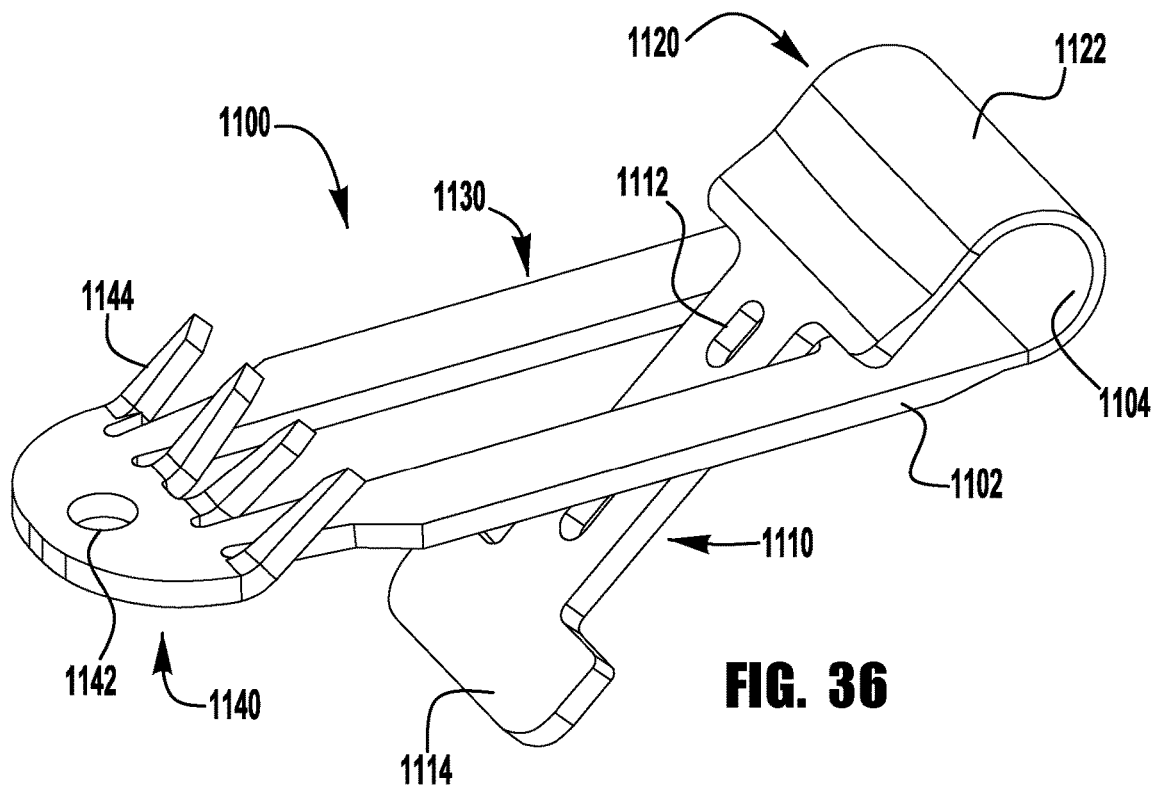
FIG. 36 shows a barbed clasp for an implantable prosthetic device according to an eighth embodiment.

Referring now to FIG. 36, an exemplary barbed clasp 1100 similar to barbed clasps 400, 500, 600 is shown. Unlike barbed clasps 400, 500, 600, however, barbed clasp 1100 is formed from a single layer of material that varies in thickness between a thick portion 1102 and a thin portion 1104. The barbed clasp 1100 includes a fixed arm 1110, a hinge portion 1120, and a moveable arm 1130. The fixed arm 1110 includes attachment holes 1112 and an optional integrated crossbar 1114. The hinge portion 1120 includes an arcuate hinge 1122 formed from the thin portion 1104. The moveable arm 1130 includes a barbed portion 1140 with barbs 1144. A suture (not shown) can be attached to an eyelet 1142 near the barbed portion 1140 to open and close the clasp 1100.

To form the barbed clasp 1100, a sheet of material is thinned to form the thin portion 1104. The shape of the clasp 1100 is then laser cut from the sheet of material so that the hinge portion 1120 is aligned with the thin portion 1104. The barbs 1144 and fixed arm 1110 are then bent into the position shown in FIG. 36 before shape setting. The optional T-shaped crossbar 1114 of the fixed arm 1110 must be twisted to insert it through the slot in the moveable arm 1130 for shape setting and to move the arms 1110, 1130 from the preloading position to a closed position. In certain embodiments, the optional T-shaped crossbar 1114 is omitted, is smaller, or is alternatively replaced with a relief in the moveable arm 1130, to facilitate ease of manufacture and shape setting. After the shape setting, the crossbar is twisted, moved back through the slot, and positioned on top of the thick portion 1102. The crossbar 1114 is positioned in generally the same manner as the crossbar 414 (see FIG. 26).

Like the clasps 400, 500 described above, the clasp 1100 can be opened fully without plastically deforming the clasp material while still providing pinching force when closed. Fewer steps are required to manufacture the clasp 1100 as compared to the clasps above, as the clasp 1100 is cut from a single sheet of material and no welding step is needed to weld layers of material together.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. An implantable prosthetic device comprising:

a body portion;

an anchor portion comprising a plurality of paddles, the paddles being extendable from a folded closed position to an open position; and a clasp attached to each of the plurality of paddles, the clasp comprising:
  a fixed arm attached to the paddle;
  a moveable arm having a barbed portion; and
  a hinge portion hingeably connecting the fixed arm to the moveable arm;
  wherein the clasp comprises a first layer and a second layer, the first and second layers formed of shape memory material;
  wherein the moveable arm is substantially parallel to the fixed arm when the clasp is in a closed position; and
  wherein a plastic limit of the material of the clasp is not exceeded when the moveable arm is opened to a fully open position about 180 degrees from the fixed arm.

2. The implantable prosthetic device according to claim 1, wherein the first and second layers are only joined in one location to allow the first and second layers to slide relative to one another during opening of the clasp.

3. The implantable prosthetic device according to claim 2, wherein the first and second layers are joined at an end of the moveable arm.

4. The implantable prosthetic device according to claim 1, wherein the barbed portion includes barbs and barb supports, and wherein the barbs are formed from the second layer and the barb supports are formed from the first layer.

5. An implantable prosthetic device comprising:
  a body portion;
  an anchor portion comprising a plurality of paddles, the paddles having an outer and inner portion and being extendable from a folded closed position to an open position; and
  a clasp attached to each of the plurality of paddles, the clasp comprising:
    a fixed arm attached to the inner portion of the paddle;
    a moveable arm having a barbed portion; and
    a hinge portion hingeably connecting the fixed arm to the moveable arm;
    wherein the clasp comprises a first layer and a second layer, the first and second layers formed of shape memory material;
    wherein the moveable arm is substantially parallel to the fixed arm when the clasp is in a closed position; and
    wherein a plastic limit of the material of the clasp is not exceeded when the moveable arm is opened to a fully open position about 180 degrees from the fixed arm.

6. An implantable prosthetic device comprising:
  a body portion;
  an anchor portion comprising a plurality of paddles, the paddles having an outer and inner portion and being extendable from a folded closed position to an open position; and
  a clasp attached to each of the plurality of paddles, the clasp comprising:
    a fixed arm attached to the inner portion of the paddle;
    a moveable arm having a barbed portion; and
    a hinge portion hingeably connecting the fixed arm to the moveable arm;
    a top layer formed from of shape memory material; and
    a bottom layer formed of shape memory material;
    wherein the moveable arm is substantially parallel to the fixed arm when the clasp is in a closed position; and
    wherein the top layer and the bottom layer are only joined together at an end of the moveable arm to allow the top and bottom layers to slide relative to one another during opening of the clasp.

7. An implantable prosthetic device comprising:
  a body portion;
  an anchor portion comprising a plurality of paddles, the paddles being extendable from a folded closed position to an open position; and
  a clasp attached to each of the plurality of paddles, the clasp comprising:
    a fixed arm attached to the paddle;
    a moveable arm having a barbed portion; and
    a hinge portion hingeably connecting the fixed arm to the moveable arm;
    a first layer formed from of shape memory material; and
    a second layer formed of shape memory material;
    wherein the moveable arm is substantially parallel to the fixed arm when the clasp is in a closed position; and
    wherein the first layer and the second layer are only joined together at an end of the moveable arm to allow the first and second layers to slide relative to one another during opening of the clasp.

8. An implantable prosthetic device comprising:
  a body portion;
  an anchor portion comprising a plurality of paddles, the paddles having an outer and inner portion and being extendable from a folded closed position to an open position; and
  a clasp attached to each of the plurality of paddles, the clasp comprising:
    a fixed arm attached to the inner portion of the paddle;
    a moveable arm comprising two side beams and a barbed portion; and
    a hinge portion hingeably connecting the fixed arm to the moveable arm, the hinge portion comprising two beam loops and each beam loop comprising:
      a center portion extending from the fixed arm; and
      an outer portion extending from the center portion to one of the two side beams of the moveable arm;
  wherein the moveable arm is substantially parallel to the fixed arm when the clasp is in a closed position.

9. An implantable prosthetic device comprising:
  a body portion;
  an anchor portion comprising a plurality of paddles, the paddles being extendable from a folded closed position to an open position; and
  a clasp attached to each of the plurality of paddles, the clasp comprising:
    a fixed arm attached to the paddle;
    a moveable arm comprising two side beams and a barbed portion; and
    a hinge portion hingeably connecting the fixed arm to the moveable arm, the hinge portion comprising two beam loops and each beam loop comprising:
      a center portion extending from the fixed arm; and
      an outer portion extending from the center portion to one of the two side beams of the moveable arm;
  wherein the moveable arm is substantially parallel to the fixed arm when the clasp is in a closed position.

10. An implantable prosthetic device comprising:
a body portion;
an anchor portion comprising a plurality of paddles, the paddles having an outer and inner portion and being extendable from a folded closed position to an open position; and
a clasp attached to each of the plurality of paddles, the clasp comprising:
  a fixed arm attached to the inner portion of the paddle;
  a moveable arm having a barbed portion; and
  a hinge portion hingeably connecting the fixed arm to the moveable arm;
  wherein the moveable arm is substantially parallel to the fixed arm when the clasp is in a closed position;
  wherein ends of the fixed and moveable arms adjacent to the hinge portion are offset from each other by an offset distance; and
  wherein a plastic limit of the material of the clasp is not exceeded when the moveable arm is opened to a fully open position about 180 degrees from the fixed arm.

11. An implantable prosthetic device comprising:
a body portion;
an anchor portion comprising a plurality of paddles, the paddles being extendable from a folded closed position to an open position; and
a clasp attached to each of the plurality of paddles, the clasp comprising:
  a fixed arm attached to the paddle;
  a moveable arm having a barbed portion; and
  a hinge portion hingeably connecting the fixed arm to the moveable arm;
  wherein the moveable arm is substantially parallel to the fixed arm when the clasp is in a closed position;
  wherein ends of the fixed and moveable arms adjacent to the hinge portion are offset from each other by an offset distance; and
  wherein a plastic limit of the material of the clasp is not exceeded when the moveable arm is opened to a fully open position about 180 degrees from the fixed arm.

* * * * *